(12) United States Patent  (10) Patent No.: US 8,188,088 B2
Stierli et al.  (45) Date of Patent: May 29, 2012

(54) ETHENYL CARBOXAMIDE DERIVATIVES USEFUL AS MICROBIOCIDES

(75) Inventors: Daniel Stierli, Stein (CH); John Taylor, Bracknell (GB); Harald Walter, Stein (CH); Paul Anthony Worthington, Bracknell (GB)

(73) Assignees: Syngenta Participations AG, Basel (CH); Syngenta Limited, Guildford, Surrey (GB)

( * ) Notice: Subject to any disclaimer, the term of this patent is extended or adjusted under 35 U.S.C. 154(b) by 136 days.

(21) Appl. No.: 12/304,177

(22) PCT Filed: Jun. 14, 2007

(86) PCT No.: PCT/EP2007/005247
§ 371 (c)(1),
(2), (4) Date: Dec. 10, 2008

(87) PCT Pub. No.: WO2007/144174
PCT Pub. Date: Dec. 21, 2007

(65) Prior Publication Data
US 2009/0318495 A1   Dec. 24, 2009

(30) Foreign Application Priority Data
Jun. 16, 2006 (EP) .................... 06012433

(51) Int. Cl.
*A61K 31/497* (2006.01)
(52) U.S. Cl. .................................. 514/254.09
(58) Field of Classification Search ............ 514/183, 514/254.09
See application file for complete search history.

(56) References Cited

FOREIGN PATENT DOCUMENTS

| | | | |
|---|---|---|---|
| EP | 1449841 A | 8/2004 | |
| EP | 1574511 A | 9/2005 | |
| WO | 01/55124 A | 8/2001 | |
| WO | 2004/018438 A | 3/2004 | |
| WO | 2006/008193 A | 1/2006 | |
| WO | 2006/008194 A1 | 1/2006 | |

*Primary Examiner* — Brandon Fetterolf
*Assistant Examiner* — Christopher R Stone
(74) *Attorney, Agent, or Firm* — R. Kody Jones

(57) ABSTRACT

Compounds of the formula (I), which are suitable for use as microbiocides, and in which A is $A_1$, or A is $A_2$, or A is $A_3$, or A is $A_4$ and B is a phenyl, naphthyl or quinolinyl group.

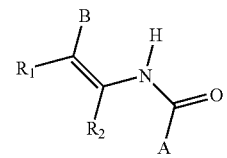

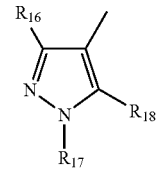

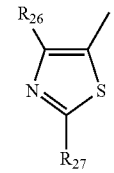

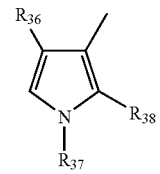

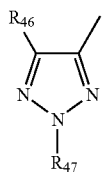

17 Claims, No Drawings

ETHENYL CARBOXAMIDE DERIVATIVES USEFUL AS MICROBIOCIDES

This application is a 371 of International Application No. PCT/EP2007/005247 filed Jun. 14, 2007, which claims priority to EP 06012433.6 filed Jun. 16, 2006, the contents of which are incorporated herein by reference.

The present invention relates to novel microbiocidally active, in particular fungicidally active, ethenyl amides. It further relates to compositions which comprise these compounds and to their use in agriculture or horticulture for controlling or preventing infestation of plants by phytopathogenic microorganisms, preferably fungi.

N-[2-(pyridinyl)ethyl]-carboxamide derivatives and their use as fungicides are described in WO 04/074280, WO 05/085238, WO 06/008193 and WO 06/008194. Similar compounds are also known in other fields of technology, for example, the use of cyanoenamines as ligands for modulating gene expression in plants or animals is described in US 2003/0109705.

It has been found that novel ethenyl amides have microbiocidal activity. The present invention thus provides compounds of the formula I

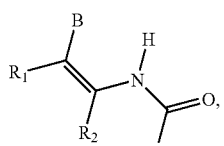

(I)

wherein $R_1$ and $R_2$ independently of each other stand for hydrogen, halogen, nitro, $C_1$-$C_6$alkyl, which is unsubstituted or substituted by one or more substituents $R_3$, $C_3$-$C_6$cycloalkyl, which is unsubstituted or substituted by one or more substituents $R_3$, $C_2$-$C_6$alkenyl, which is unsubstituted or substituted by one or more substituents $R_3$ or $C_2$-$C_6$alkynyl, which is unsubstituted or substituted by one or more substituents $R_3$;

each $R_3$ independently of each other stand for halogen, nitro, $C_1$-$C_6$alkoxy, $C_1$-$C_6$halogenalkoxy, $C_3$-$C_6$cycloalkyl, $C_1$-$C_6$alkylthio, $C_1$-$C_6$halogenalkylthio, —C(H)=N(O—$C_1$-$C_6$alkyl) or —C($C_1$-$C_6$alkyl)=N(O—$C_1$-$C_6$alkyl);

or $R_1$ and $R_2$ together with the carbon atoms to which they are attached form a 5-, 6- or 7-membered ring, wherein said ring is partially saturated and wherein 1, 2 or 3 carbon atoms of said ring may be replaced by oxygen atoms, nitrogen atoms and/or sulfur atoms and wherein said ring is unsubstituted or substituted by one or more substituents $R_4$;

each substituent $R_4$ independently of each other stands for halogen, nitro, $C_1$-$C_6$alkyl, which is unsubstituted or substituted by one or more substituents $R_5$, $C_3$-$C_6$cycloalkyl, which is unsubstituted or substituted by one or more substituents $R_5$, $C_2$-$C_6$alkenyl, which is unsubstituted or substituted by one or more substituents $R_5$ or $C_2$-$C_6$alkynyl, which is unsubstituted or substituted by one or more substituents $R_5$;

each $R_5$ independently of each other stand for halogen, nitro, $C_1$-$C_6$alkoxy, $C_1$-$C_6$halogenalkoxy, $C_3$-$C_6$cycloalkyl, $C_1$-$C_6$alkylthio, $C_1$-$C_6$halogenalkylthio, —C(H)=N(O—$C_1$-$C_6$alkyl) or —C($C_1$-$C_6$alkyl)=N(O—$C_1$-$C_6$alkyl);

A is $A_1$

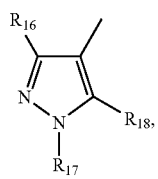

($A_1$)

in which $R_{16}$ is halogenmethyl;
$R_{17}$ is $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl; and
$R_{18}$ is hydrogen, halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

or A is $A_2$

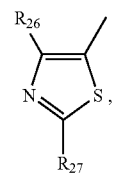

($A_2$)

in which $R_{26}$ is halogenmethyl; and
$R_{27}$ is $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl;

or A is $A_3$

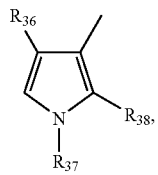

($A_3$)

in which $R_{36}$ is halogenmethyl;
$R_{37}$ is $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl; and
$R_{38}$ is hydrogen, halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

or A is $A_4$

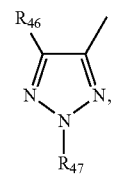

($A_4$)

in which $R_{46}$ is halogenmethyl; and
$R_{47}$ is $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl;

B is a phenyl, naphthyl or quinolinyl group, which is substituted by one or more substituents $R_7$;

each substituent $R_7$ independently of each other stands for halogen, $C_1$-$C_6$haloalkoxy, $C_1$-$C_6$haloalkylthio, cyano, nitro, —C(H)=N(O—$C_1$-$C_6$alkyl), —C($C_1$-$C_6$alkyl)=N(O—$C_1$-$C_6$alkyl), $C_1$-$C_6$alkyl, which is unsubstituted or substituted by one or more substituents $R_8$, $C_3$-$C_6$cycloalkyl, which is unsubstituted or substituted by one or more substituents $R_8$, $C_6$-$C_{14}$bicycloalkyl, which is unsubstituted or substituted by one or more substituents $R_8$, $C_2$-$C_6$alkenyl, which is unsubstituted or substituted by one or more substituents $R_8$, $C_2$-$C_6$alkynyl, which is unsubstituted or substituted by one or more substituents $R_8$, phenyl, which is unsubstituted or substituted by one or more substituents $R_8$ or heteroaryl, which is unsubstituted or substituted by one or more substituents $R_8$;

each $R_8$ is independently of each other halogen, cyano, nitro, $C_1$-$C_6$alkoxy, $C_1$-$C_6$halogenalkoxy, $C_1$-$C_6$alkylthio, $C_1$-$C_6$halogenalkylthio, $C_3$-$C_6$alkenyloxy, $C_3$-$C_6$alkynyloxy, —C(H)=N(O—$C_1$-$C_6$alkyl) or —C($C_1$-$C_6$alkyl)=N(O—$C_1$-$C_6$alkyl);

and isomers and tautomers of these compounds.

The alkyl groups occurring in the definitions of the substituents can be straight-chain or branched and are, for example, methyl, ethyl, n-propyl, n-butyl, n-pentyl, n-hexyl, isopropyl, n-butyl, sec-butyl, isobutyl or tert-butyl. Alkoxy, alkenyl and alkynyl radicals are derived from the alkyl radicals mentioned. The alkenyl and alkynyl groups can be mono- or di-unsaturated.

The cycloalkyl groups occurring in the definitions of the substituents are, for example, cyclopropyl, cyclobutyl, cyclopentyl or cyclohexyl.

The bicycloalkyl groups occurring in the definitions of the substituents are, depending on the ring size, bicyclo[2.1.1]hexane, bicyclo[2.2.1]heptane, bicyclo[2.2.2]octane, bicyclo[3.2.1]octane, bicyclo[3.2.2]nonane, bicyclo[4.2.2]decane, bicyclo[4.3.2]undecane, adamantane and the like.

Halogen is generally fluorine, chlorine, bromine or iodine, preferably fluorine, bromine or chlorine. This also applies, correspondingly, to halogen in combination with other meanings, such as halogenalkyl or halogenalkoxy.

Halogenalkyl groups preferably have a chain length of from 1 to 4 carbon atoms. Halogenalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Suitable halogenalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl.

Suitable halogenalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoro-propynyl and 4,4,4-trifluorobut-2-yn-1-yl.

Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio is, for example, methylthio, ethylthio, propylthio, isopropylthio, n-butylthio, isobutylthio, sec-butylthio or tert-butylthio, preferably methylthio and ethylthio.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

In the context of the present invention "substituted by one or more substituents" in the definition of substituents $R_1$, $R_2$, $R_4$ and $R_7$, means typically, depending on the chemical structure of substituents $R_1$, $R_2$, $R_4$ and $R_7$, monosubstituted to nine-times substituted, preferably monosubstituted to five-times substituted, more preferably mono-, double- or triple-substituted.

In the context of the present invention "substituted by one or more substituents" in the definition of substituent B, means typically, depending on the chemical structure of substituent B, monosubstituted to seven-times substituted, preferably monosubstituted to five-times substituted, more preferably mono-, double- or triple-substituted.

The compounds of the formula I (Z-form) occur also in the isomeric form $I_1$ (E-form):

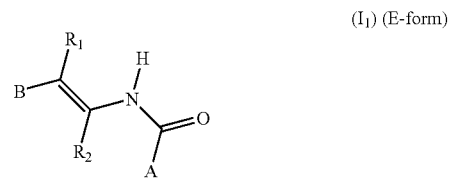

($I_1$) (E-form)

The invention also covers the isomeric form $I_1$.

Compounds of the formula IA

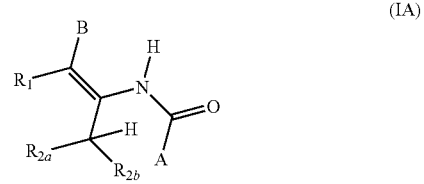

(IA)

wherein B, $R_1$ and A are as defined under formula I and $R_{2a}$ and $R_{2b}$ are each independently hydrogen or $C_1$-$C_5$alkyl, which is unsubstituted or substituted by one or more substituents $R_3$, $C_2$-$C_5$alkenyl, which is unsubstituted or substituted by one or more substituents $R_3$ or $C_2$-$C_5$alkynyl, which is unsubstituted or substituted by one or more substituents $R_3$;

or $R_1$ and $R_{2a}$ together with the carbon atoms to which they are attached form a 5-, 6- or 7-membered ring, wherein said ring is partially saturated and wherein 1, 2 or 3 carbon atoms of said ring may be replaced by oxygen atoms, nitrogen atoms and/or sulfur atoms and wherein said ring is unsubstituted or substituted by one or more substituents $R_4$; occur also in the isomeric form $IA_1$

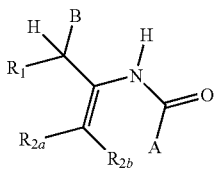
(IA$_I$)

The invention also covers the isomeric form IA$_I$.

Compounds of the formula I exist also in tautomeric forms, such as, for example the tautomeric form I$_{II}$:

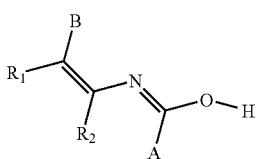
(I$_{II}$)

The invention also covers the tautomeric form I$_{II}$ and all tautomeric forms of compounds of formula I$_I$, IA and IA$_I$ or mixtures of any of these compounds in any ratio.

In a preferred group of compounds $R_1$ and $R_2$ independently of each other stand for hydrogen, halogen or $C_1$-$C_6$alkyl, which is unsubstituted or substituted by one or more substituents $R_3$, or $R_1$ and $R_2$ together with the carbon atoms to which they are attached form a 5-, 6- or 7-membered ring, wherein said ring is partially saturated and wherein said ring is unsubstituted or substituted by one or more substituents $R_4$.

In a preferred group of compounds $R_1$ and $R_2$ independently of each other stand for hydrogen, halogen or $C_1$-$C_6$alkyl, which is unsubstituted or substituted by one or more substituents $R_3$, or $R_1$ and $R_2$ together with the carbon atoms to which they are attached form a 5-, 6- or 7-membered ring, wherein said ring is partially saturated and wherein said ring is unsubstituted or substituted by one or more substituents $R_4$.

In a preferred group of compounds $R_1$ and $R_2$ independently of each other stand for hydrogen, halogen or $C_1$-$C_6$alkyl, which is unsubstituted or substituted by one or more substituents selected from halogen, $C_1$-$C_6$alkoxy and $C_1$-$C_6$halogenalkoxy; or $R_1$ and $R_2$ together with the carbon atoms to which they are attached form a 5-, 6- or 7-membered ring, wherein said ring is partially saturated and wherein said ring is unsubstituted or substituted by one or more substituents selected from halogen, $C_1$-$C_6$alkoxy and $C_1$-$C_6$halogenalkoxy.

In a preferred group of compounds $R_1$ and $R_2$ independently of each other stand for hydrogen, halogen or $C_1$-$C_6$alkyl, which is unsubstituted or substituted by one or more substituents selected from halogen, cyano, $C_1$-$C_6$alkoxy and $C_1$-$C_6$halogenalkoxy; more preferably $R_1$ and $R_2$ independently of each other stands for hydrogen, halogen or $C_1$-$C_6$alkyl, which is unsubstituted or substituted by one or more substituents selected from halogen and $C_1$-$C_6$alkoxy; most preferably $R_1$ and $R_2$ independently of each other stands for hydrogen, halogen, or $C_1$-$C_6$alkyl.

In another preferred group of compounds $R_1$ and $R_2$ with the carbon atoms to which they are attached form a 5-, 6- or 7-membered ring, wherein said ring is partially saturated and wherein said ring is unsubstituted or substituted by one or more substituents selected from halogen, $C_1$-$C_6$alkoxy and $C_1$-$C_6$halogenalkoxy.

In a preferred group of compounds A is $A_1$.
In another preferred group of compounds A is $A_2$.
In another preferred group of compounds A is $A_3$.
In another preferred group of compounds A is $A_4$.
In a particular preferred group of compounds A is $A_1$, wherein $R_{18}$ is hydrogen. In another particular preferred group of compounds A is $A_1$, wherein $R_{16}$ is halomethyl, preferably $R_{16}$ is selected from $CF_3$, $CF_2H$ and $CFH_2$; $R_{17}$ is $C_1$-$C_4$alkyl; and $R_{18}$ is hydrogen or halogen, preferably hydrogen.

In another particular preferred group of compounds A is $A_2$, wherein $R_{26}$ is halomethyl, preferably $R_{26}$ is selected from $CF_3$, $CF_2H$ and $CFH_2$; and $R_{27}$ is $C_1$-$C_4$alkyl.

In yet another particular preferred group of compounds A is $A_3$, wherein $R_{36}$ is halomethyl, preferably $R_{36}$ is selected from $CF_3$, $CF_2H$ and $CFH_2$; $R_{37}$ is $C_1$-$C_4$alkyl; and $R_{38}$ is hydrogen or halogen.

In yet another particular preferred group of compounds A is $A_4$, wherein $R_{46}$ halomethyl, preferably $R_{46}$ is selected from $CF_3$, $CF_2H$ and $CFH_2$; and $R_{47}$ is $C_1$-$C_4$alkyl.

One embodiment of the invention is represented by compounds, wherein B is a phenyl group, which is substituted by one or more substituents $R_7$.

Within said embodiment, preferably B is a phenyl group, which is substituted by one, two or three substituents $R_7$; more preferably B is a phenyl group, which is substituted by one or two substituents $R_7$.

Also preferably, B is a phenyl group, that is substituted by at least one substituent $R_7$ in the para-position.

In a preferred group of compounds each substituent $R_7$ independently of each other stands for halogen, $C_1$-$C_6$haloalkoxy, $C_1$-$C_6$haloalkylthio, cyano, nitro, —C(H)=N(O—$C_1$-$C_6$alkyl), —C($C_1$-$C_6$alkyl)=N(O—$C_1$-$C_6$alkyl), $C_1$-$C_6$alkyl, which is unsubstituted or substituted by one or more substituents $R_8$, $C_2$-$C_6$alkenyl, which is unsubstituted or substituted by one or more substituents $R_8$ or $C_2$-$C_6$alkynyl, which is unsubstituted or substituted by one or more substituents $R_8$.

In a preferred group of compounds each substituent $R_7$ independently of each other stands for halogen, $C_1$-$C_6$alkyl, which is unsubstituted or substituted by one or more substituents selected from halogen and $C_1$-$C_6$alkoxy or $C_2$-$C_6$alkynyl, which is unsubstituted or substituted by one or more substituents selected from halogen and $C_1$-$C_6$alkoxy.

In a preferred group of compounds, B is $B_1$

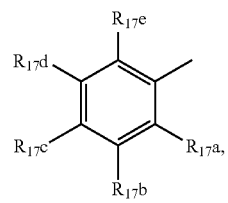
($B_1$)

in which $R_{17a}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens; $R_{17b}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens; $R_{17c}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens; $R_{17d}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens; $R_{17e}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens; provided that at least one of $R_{17a}$, $R_{17b}$, $R_{17c}$, $R_{17d}$ and $R_{17e}$ is not hydrogen.

In one embodiment of the invention, $R_{17b}$ and $R_{17d}$ is hydrogen; and $R_{17a}$, $R_{17c}$ and $R_{17e}$ independently of one another are selected from hydrogen, halogen, cyano, $C_2$-$C_6$alkynyl, $C_1$-$C_6$halogenalkyl, $C_1$-$C_6$halogenalkoxy or phenyl, which is substituted halogen; provided that at least one of $R_{17a}$, $R_{17c}$ and $R_{17e}$ is not hydrogen.

In one embodiment of the invention, $R_{17b}$ and $R_{17d}$ is hydrogen; and $R_{17a}$, $R_{17c}$ and $R_{17e}$ independently of one another are selected from hydrogen, halogen, $C_2$-$C_6$alkynyl or $C_1$-$C_6$halogenalkyl; provided that at least one of $R_{17a}$, $R_{17c}$ and $R_{17e}$ is not hydrogen.

Another embodiment of the invention is represented by compounds, wherein B is a naphthyl or quinolinyl group, which is substituted by one or more substituents $R_7$.

Another embodiment of the invention is represented by compounds, wherein B is a naphthyl group, which is substituted by one or more substituents $R_7$.

Within said embodiment, preferably B is a naphthyl group, which is substituted by one or two substituents $R_7$. Within said embodiment, in a preferred group of compounds each substituent $R_7$ independently of each other stands for halogen, $C_1$-$C_6$haloalkoxy, $C_1$-$C_6$alkyl, which is unsubstituted or substituted by one or more substituents selected from halogen and $C_1$-$C_6$alkoxy; $C_2$-$C_6$alkynyl, which is unsubstituted or substituted by one or more substituents selected from halogen and $C_1$-$C_6$alkoxy; or phenyl, which is unsubstituted or substituted by one or more halogens.

Another embodiment of the invention is represented by compounds, wherein B is a quinolinyl group, which is substituted by one or two substituents $R_7$. Within said embodiment, in a preferred group of compounds each substituent $R_7$ independently of each other stands for halogen, $C_1$-$C_6$haloalkoxy, $C_1$-$C_6$alkyl, which is unsubstituted or substituted by one or more substituents selected from halogen and $C_1$-$C_6$alkoxy; $C_2$-$C_6$alkynyl, which is unsubstituted or substituted by one or more substituents selected from halogen and $C_1$-$C_6$alkoxy; or phenyl, which is unsubstituted or substituted by one or more halogens.

Compounds of formula I may be prepared by reaction scheme 1.

Scheme 1:

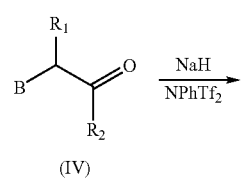

(IV)

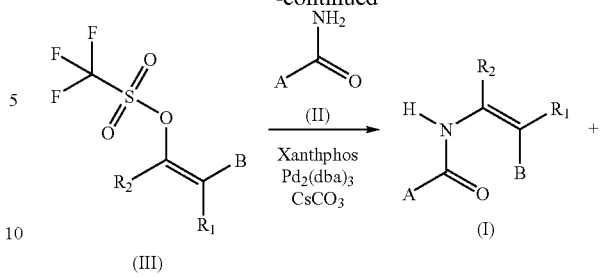

Carbonyl compounds of formula IV, wherein $R_1$, $R_2$ and B are as defined under formula I, can be transformed into enol triflates of formula III, wherein $R_1$, $R_2$ and B are as defined under formula I, by using standard methodology, such as for example reaction with NaH and NPhTf$_2$. Said methodology is described in *J. Am. Chem. Soc.* 1991, 113, 8975; *J. Org. Chem.* 1989, 54, 4975 and *Tetrahedron Lett.* 1983, 979. Reaction temperatures are between −20° C. and 30° C., suitable solvents are ethers such as THF, diethyl ether, or dioxane. Palladium-catalyzed amidation of the enol triflates of formula III with primary amides of formula II, wherein A is as defined under formula I gives the compounds of formula I and the isomeric compounds of formula I$_I$. Usually both isomers are obtained. Reaction temperatures are between 10° C. and 80° C. and a suitable solvent for this reaction is, for example, dioxane. Further reaction parameters are described in *Organic Lett.* 2003, 5, 4749-4752.

Compounds of formula IV may be prepared by reaction scheme 2.

Scheme 2:

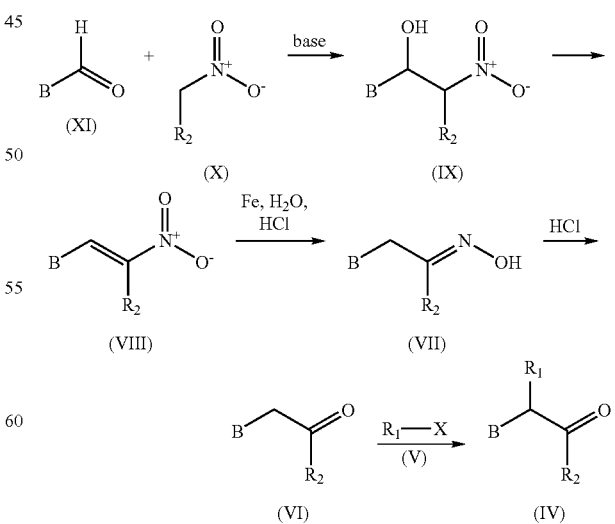

Carbonyl compounds of formula (XI), in which B is as defined under formula I can be reacted with nitroalkanes of formula X, in which $R_2$ is as defined under formula I to give 2-nitro alcohol compounds of formula IX, in which B and $R_2$ are as defined under formula I, via the so-called "Henry-reaction" (nitroaldol-reaction) according to (a) Baer, H. H., Urbas, L. *The chemistry of the nitro and nitroso groups*; Feuer, H., Ed.; *Interscience: New York*, 1970; Vol. 2, pp 75-20; (b) Schickh, G.; Apel, H. G. *Methoden der Organischen Chemie (Houben-Weyl Stuttgart*, 1971; Vol. 10/1, pp 9-462; (c) Kabalka, G. W.; Varma, R. s. *Org. Prep. Proc. Int* 1987, 283-328; or (d) Luzzio, F. A. *Tetrahedron* 2001, 57, 915-945. Subsequent dehydration gives nitroalkenes of formula VIII, in which B and $R_2$ are as defined under formula I. Such a dehydration step is described, for example, in *Org. Synthesis Coll Vol I*, 413, (1941). The above-mentioned reactions are carried out at temperatures of between 0-80° C. in convenient protic and aprotic solvents, but can be also performed under solvent-free conditions. Convenient bases described in the literature include alkali metal hydroxides, alkaline earth oxides, carbonates, bicarbonates, alkoxides and quarternary ammonium salts. The nitroalkenes of formula VIII can be reduced with iron and hydrochloric acid to give oximes of formula VII, in which B and $R_2$ are as defined under formula I. Said oximes can be hydrolyzed to ketones of formula VI, in which B and $R_2$ are as defined under formula I, as it is described, for example, in *J. Am. Chem. Soc.* 65, 1180 (1943) and *Synthetic Commun.*, 35, 913-922, 2005. The reaction is carried out at temperatures between 40-100° C. in a convenient organic solvent such as methanol, ethanol, tert-butanol, trifluoroethanol or dioxane. The alkylation of the ketone of formula VI with a compound of formula V, in which $R_1$ is as defined under formula I and X is a leaving group, such as halogen, mesylate or tosylate, in the presence of a base yields the desired α-alkylated ketone of formula IV, wherein B, $R_1$ and $R_2$ are as defined under formula I. This reaction is advantageously carried out in aprotic inert organic solvents. Such solvents are hydrocarbons such as benzene, toluene, xylene or cyclohexane, ethers such as diethyl ether, ethylene glycol dimethyl ether, diethylene glycol dimethyl ether, tetrahydrofuran or dioxane, amides such as N,N-dimethylformamide, diethylformamide or N-methylpyrrolidinone. The reaction temperatures are between −20° C. and +120° C. Suitable bases are inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

Compounds of formula IB may be prepared by reaction scheme 3.

Scheme 3:

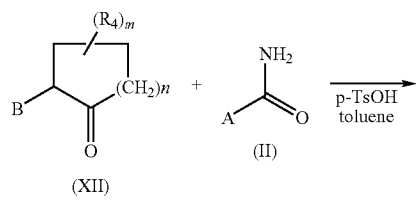

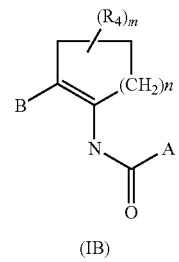

Cycloalkenyl compounds of formula IB, wherein $R_4$, A and B are as defined under formula I and n and m are 1 to 3, may be prepared by condensation of 2-arylcycloalkanones of formula XII, wherein $R_4$ and B are as defined under formula I and n and m are 1 to 3, with a primary amide of formula II, wherein A is as defined under formula I. Such condensation reactions are described, for example, in *J. Org. Chem.* 1995, 60, 4324-4330. The reaction is carried out in a convenient solvent at reflux temperature with an acidic catalyst and azeotropic removal of water. Suitable solvents are toluene or xylene. Para-toluenesulfonic acid (PTSA) and Amberlyst-15 resin can be used as acid catalysts.

Compounds of formula II may be prepared by reaction scheme 4.

Scheme 4:

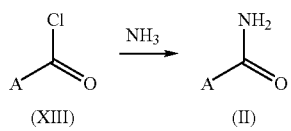

Compounds of formula XIII, wherein A is as defined under formula I, be reacted with ammonia to give the compounds of formula II by using known methodology.

For preparing all further compounds of the formula I functionalized according to the definitions of A, B, $R_1$ and $R_2$, there are a large number of suitable known standard methods, such as alkylation, halogenation, acylation, amidation, oximation, oxidation and reduction. The choice of the preparation methods which are suitable are depending on the properties (reactivity) of the substituents in the intermediates.

The compounds of the formula XIII are known and some of them are commercially available. They can be prepared analogously as described, for example, in WO 00/09482, WO 02/38542, WO 04/018438, EP-0-589-301, WO 93/11117 and Arch. Pharm. Res. 2000, 23(4), 315-323.

The compounds of formula V, X, XI and XII are known and are commercially available or can be prepared according to the above-mentioned references or according to methods known in the art.

The reactions leading to compounds of the formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at room temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

The compounds of formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

The compounds I and, where appropriate, the tautomers thereof, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereo-isomeric mixtures or racemate mixtures of compounds I, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomeric mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisams, such as fungi, bacteria or viruses.

The invention relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis, Pyricularia, Helminthosporium, Fusarium, Septoria, Cercospora* and *Alternaria*) and *Basidiomycetes* (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the the application (location, timing, application method) and can, owing to these parameters, vary within wide limits.

Surprisingly, it has now been found that the compounds of formula I can also be used in methods of protecting crops of useful plants against attack by phytopathogenic organisms as well as the treatment of crops of useful plants infested by phytopathogenic organisms comprising administering a combination of glyphosate and at least one compound of formula I to the plant or locus thereof, wherein the plant is resistant or sensitive to glyphosate.

Said methods may provide unexpectedly improved control of diseases compared to using the compounds of formula I in the absence of glyphosate. Said methods may be effective at enhancing the control of disease by compounds of formula I. While the mixture of glyphosate and at least one compound of formula I may increase the disease spectrum controlled, at least in part, by the compound of formula I, an increase in the activity of the compound of formula I on disease species already known to be controlled to some degree by the compound of formula I can also be the effect observed.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

Surprisingly, it has now been found that the compounds of formula I, or a pharmaceutical salt thereof, described above have also an advantageous spectrum of activity for the treatment and/or prevention of microbial infection in an animal.

"Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula I in the manufacture of a medicament for use in the treatment and/or prevention of microbial infection in an animal. There is also provided the use of a compound of formula I as a pharmaceutical agent. There is also provided the use of a compound of formula I as an antimicrobial agent in the treatment of an animal. According to the present invention there is also provided a pharmaceutical composition comprising as an active ingredient a compound of formula I, or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula I are effective against various microbial species able to cause a microbial infection in an animal. Examples of such microbial species are those causing Aspergillosis such as *Aspergillus fumigatus, A. flavus, A. terrus, A. nidulans* and *A. niger*, those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucorpusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in more detail without limiting it.

PREPARATION EXAMPLES

Example P1

Preparation of 3-difluoromethyl-1-methyl-1H-pyrazole-4-carboxylic acid [(E/Z)-2-(4-chlorophenyl)-1-methyl-vinyl]-amide (Compound No. 1.007)

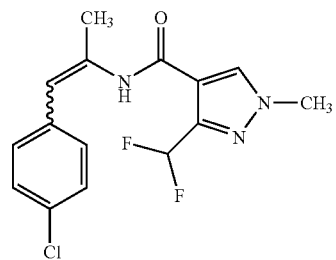

a) Preparation of trifluoro-methanesulfonic acid-2-(4-chloro-phenyl)-1-methyl-vinyl ester

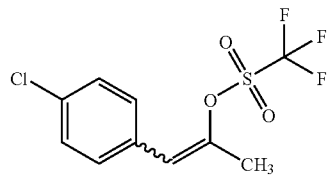

4-Chlorophenylacetone (1.0 g, 5.9 mmol) was added to a stirred suspension of sodium hydride (515 mg of 55-65 wt %, 11.8 mmol) in THF (15 ml) at 0° C. The reaction mixture was stirred for 1 hour, then N-phenyl-(bis)-trifluoromethanesulfonamide (2.5 g, 7.08 mmol) was added. The reaction mixture was stirred for 3 hours at ambient temperature. MeOtBu (20 ml) and ethanol (1 ml) was added. After this, water (20 ml) was added and the layers were separated. The aqueous layer was extracted with MeOtBu (20 ml). The combined organic layers were washed with water (20 ml) and 10% sodium chloride solution (20 ml), dried over MgSO$_4$ and concentrated in vacuo. The concentrate was purified by flash chromatography over silicagel (eluent: hexane/ethylacetate 9:1). 1.5 g (84% of theory) of a mixture of E- and Z-isomers of trifluoro-methanesulfonic acid-2-(4-chloro-phenyl)-1-methyl-vinyl ester was obtained in the form of a colourless oil.

$^1$H NMR (400 MHz, CDCl$_3$): δ 6.57 (s, 1H, (Z-form), 6.1 (s, 1H, (E-form)), 2.27 (s, 3H, (E-form)), 2.25 (s, 3H, (Z-form)).

b) Preparation of 3-difluoromethyl-1-methyl-1H-pyrazole-4-carboxylic acid [(E/Z)-2-(4-chlorophenyl)-1-methyl-vinyl]-amide (Compound No. 1.007)

Cs$_2$CO$_3$ (301 mg, 0.92 mmol), 3-difluoromethyl-1-methyl-1H-pyrazole-4-carboxylic acid amide (150 mg, 0.86 mmol), Xantphos (38 mg, 0.06 mmol) and Pd$_2$(dba)$_3$ (20 mg, 0.02 mmol) were added to a solution of the enol triflates as prepared under example 1a) (200 mg, 0.66 mmol) in dioxane (4 ml) at ambient temperature. The mixture was stirred under nitrogen for 15 hours atmosphere at 50° C. The mixture was filtered, concentrated and purified by flash chromatography over silicagel (eluent: hexane/ethylacetate 8:2). A mixture of 3-difluoromethyl-1-methyl-1H-pyrazole-4-carboxylic acid [(E)-2-(4-chlorophenyl)-1-methyl-vinyl]-amide and 3-difluoromethyl-1-methyl-1H-pyrazole-4-carboxylic acid [(Z)-2-(4-chlorophenyl)-1-methyl-vinyl]-amide was obtained.

$^1$H NMR (400 MHz, CDCl$_3$): E-isomer δ 2.12 (d, 3H, CH$_3$), 3.93 (s, 3H, CH$_3$), 6.85 (t, 1H, CHF$_2$, J=55 Hz), 7.18 (m, 2H, ArH), 7.30 (m, 2H, ArH), 7.30 (s, 1H), 7.49 (s, 1H, NH), 7.97 (s, 1H, pyrazole-H); Z-isomer δ 2.34 (d, 3H, CH$_3$), 3.98 (s, 3H, CH$_3$), 5.83 (s, 1H), 6.83 (t, 1H, CHF$_2$, J=55 Hz), 7.19 (m, 2H, ArH), 7.26 (m, 2H, ArH), 7.64 (s, 1H, NH), 7.84 (s, 1H, pyrazole-H).

Example P2

Preparation of 1-Methyl-3-trifluoromethyl-1H-pyrazole-4-carboxylic acid [2-(4-chlorophenyl)-cyclohex-1-enyl]-amide (Compound No. 2.025)

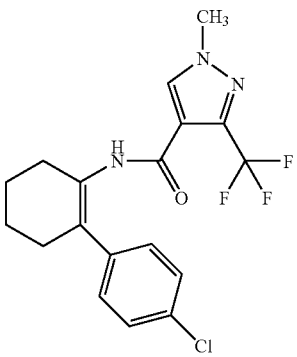

0.521 g 2-(4-chlorophenyl)-cyclohexanone (prepared as described in J. Org. Chem. 70, 2005, page 2967) and 0.482 g 1-methyl-3-trifluoromethyl-1H-pyrazole-4-carboxylic acid amide were suspended with 5 mg p-toluenesulfonic acid in 20 ml toluene and heated to reflux temperature of the solvent for 24 hours under continuos removal of water. The reaction mixture was washed with 5% sodium bicarbonate and water, dried and the solvent was removed under vacuum. The reaction product was purified by chromatography on a silica gel column (eluent: ethylacetate:hexane 1:1). 0.55 g 1-Methyl-3-trifluoromethyl-1H-pyrazole-4-carboxylic acid [2-(4-chlorophenyl)-cyclohex-1-enyl]-amide was obtained in the form of crystals (m.p. 145-148° C.).

Example P3

Preparation of 3-difluoromethyl-1-methyl-1H-pyrazole-4-carboxylic acid [2-(4-chloro-phenyl)-cyclopent-1-enyl]-amide (Compound No. 1.024)

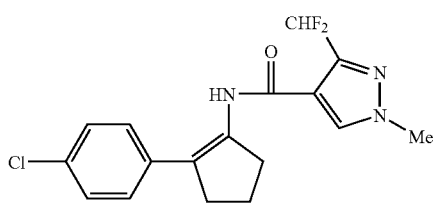

a) Preparation of 2-(4'chlorophenyl)cyclopent-2-enone

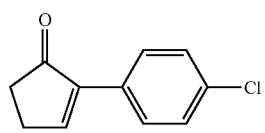

4.8 g 2-Iodo-cyclopent-2-enone (prepared as described in Org. Lett. 6, 2004, page 3289), 5.4 g 4-chlorophenylboronic acid, 8.5 g silver(I)oxide, 0.425 g triphenylarsine and 0.265 g Pd(C$_6$H$_5$CN)$_2$Cl$_2$ were added to 90 ml tetrahydrofurane and 20 ml water. The reaction mixture was stirred under nitrogen atmosphere for 16 hours. The reaction mixture was diluted with ammonium chloride, filtered and extracted twice with ethyl acetate. The residue was purified by chromatography and the solvent was evaporated. 3.44 g 2-(4'chlorophenyl) cyclopent-2-enone were obtained (m.p. 71-72° C.).

b) Preparation of trifluoro-methanesulfonic acid-2-(4-chloro-phenyl)-1-methyl-vinyl ester

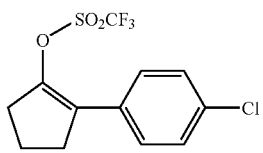

0.5 g of the product prepared as described under example 3a) were dissolved in 15 ml dichloromethane and cooled to −78° C. 2.85 ml of a 1M solution of sodium selectride was added dropwise. The reaction mixture was stirred for 2 hours at −78° C. 1 g N,N-Bis(trifluormethylsulfonyl)aniline was added and the mixture was warmed to ambient temperature. Water was added, the reaction mixture was extracted with dichloromethane, washed with water and dried. After removal of the solvent, the reaction mixture was chromatographed on silica gel (hexane:ethyl acetate 3:1). 0.61 g of the enoltriflate was obtained. This reaction product was used directly without further purification.

c) Preparation of 1,3-Dimethyl-1H-pyrazole-4-carboxylic acid [2-(4-chloro-phenyl)-cyclopent-1-enyl]-amide (Compound No. 1.024)

The enoltriflate prepared as described under example 3b) was dissolved under nitrogen atmosphere in 12 ml dioxane, 0.85 g cesium carbonate and 0.425 g 1-Methyl-3-difluormethyl-4-pyrazolcarboxamide was added. 0.19 g Xantphos® and 0.1 g Pd$_2$(dba)$_3$ were added and the resulting suspension stirred under nitrogen atmosphere for 16 hours at 50° C. The reaction mixture was filtered, washed with ethyl acetate, the solvent was removed and the reaction product was purified by chromatography on silica gel (hexane:ethyl acetate 3:1). 0.4 g of 1,3-Dimethyl-1H-pyrazole-4-carboxylic acid [2-(4-chloro-phenyl)-cyclopent-1-enyl]-amide was obtained (m.p. 103-105° C.).

Tables 1 to 6: Compounds of Formula IC

The invention is further illustrated by the preferred individual compounds of formula IC listed below in Tables 1 to 6. Characterising data is given in Table 13.

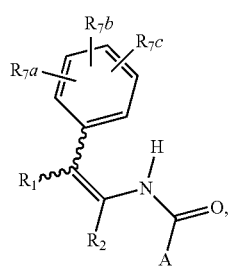

(IC)

Each of Tables 1 to 6, which follow the Table Y below, comprises 256 compounds of the formula IC in which $R_1$, $R_2$, $R_{7a}$, $R_{7b}$ and $R_{7c}$ have the values given in Table Y and A has the value given in the relevant Table 1 to 6. Thus Table 1 corresponds to Table Y when Y is 1 and A has the value given under the Table 1 heading, Table 2 corresponds to Table Y when Y is 2 and A has the value given under the Table 2 heading, and so on for Tables 3 to 6. All compounds of formula IC occur in at least two different isomeric forms as they are described for compounds of formula I as compounds of formula I (Z-form) and compounds of formula I$_f$ (E-form). For example, compounds no. Y.001 occurs in the two different isomeric forms Y.001 (Z-form) and Y.001 (E-form):

Y.001 (Z-form)

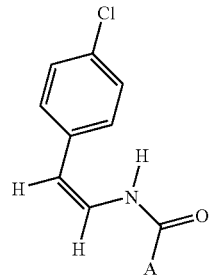

Y.001 (E-form)

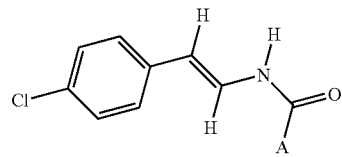

Some other compounds of formula IC, such as, for example compounds no. Y.007, Y.019, Y.033 and Y.045 amongst others, occur in three different isomeric forms. For example, compounds no. Y.007 occur in the three different isomeric forms Y.007 (Z-form), Y.007 (E-form) and Y.007 (3):

Y.007 (Z-form)

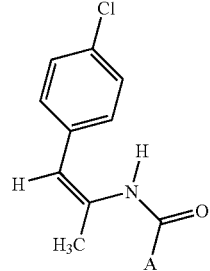

Y.007 (E-form)

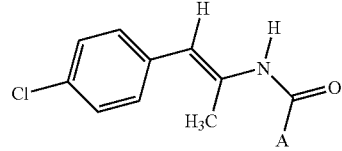

Y.007 (3)

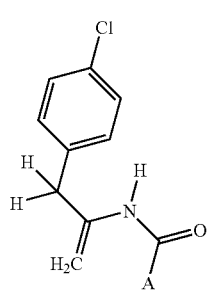

Other compounds of formula IC occur in more than three isomeric forms. For example, compounds no. Y.008 to Y.018 occur in more than three different isomeric forms.

TABLE Y

| Comp. No. | $R_1$ | $R_2$ | $R_{7a}$ | $R_{7b}$ | $R_{7c}$ |
|---|---|---|---|---|---|
| Y.001 | H | H | 4-Cl | H | H |
| Y.002 | $CH_3$ | H | 4-Cl | H | H |
| Y.003 | $CH_2CH_3$ | H | 4-Cl | H | H |
| Y.004 | $CH(CH_3)_2$ | H | 4-Cl | H | H |
| Y.005 | $(CH_2)_2CH_3$ | H | 4-Cl | H | H |
| Y.006 | $(CH_2)_3CH_3$ | H | 4-Cl | H | H |
| Y.007 | H | $CH_3$ | 4-Cl | H | H |
| Y.008 | $CH_3$ | $CH_3$ | 4-Cl | H | H |
| Y.009 | $CH_2CH_3$ | $CH_3$ | 4-Cl | H | H |
| Y.010 | $CH(CH_3)_2$ | $CH_3$ | 4-Cl | H | H |
| Y.011 | $(CH_2)_2CH_3$ | $CH_3$ | 4-Cl | H | H |
| Y.012 | $(CH_2)_3CH_3$ | $CH_3$ | 4-Cl | H | H |
| Y.013 | H | $CH_2CH_3$ | 4-Cl | H | H |
| Y.014 | $CH_3$ | $CH_2CH_3$ | 4-Cl | H | H |
| Y.015 | $CH_2CH_3$ | $CH_2CH_3$ | 4-Cl | H | H |
| Y.016 | $CH(CH_3)_2$ | $CH_2CH_3$ | 4-Cl | H | H |
| Y.017 | $(CH_2)_2CH_3$ | $CH_2CH_3$ | 4-Cl | H | H |
| Y.018 | $(CH_2)_3CH_3$ | $CH_2CH_3$ | 4-Cl | H | H |
| Y.019 | H | $CH(CH_3)_2$ | 4-Cl | H | H |
| Y.020 | $CH_3$ | $CH(CH_3)_2$ | 4-Cl | H | H |
| Y.021 | $CH_2CH_3$ | $CH(CH_3)_2$ | 4-Cl | H | H |
| Y.022 | $CH(CH_3)_2$ | $CH(CH_3)_2$ | 4-Cl | H | H |
| Y.023 | $(CH_2)_2CH_3$ | $CH(CH_3)_2$ | 4-Cl | H | H |
| Y.024 | $(CH_2)_3$ | | 4-Cl | H | H |
| Y.025 | $(CH_2)_4$ | | 4-Cl | H | H |
| Y.026 | $(CH_2)_5$ | | 4-Cl | H | H |
| Y.027 | H | H | $4-CF_3$ | H | H |
| Y.028 | $CH_3$ | H | $4-CF_3$ | H | H |
| Y.029 | $CH_2CH_3$ | H | $4-CF_3$ | H | H |
| Y.030 | $CH(CH_3)_2$ | H | $4-CF_3$ | H | H |
| Y.031 | $(CH_2)_2CH_3$ | H | $4-CF_3$ | H | H |
| Y.032 | $(CH_2)_3CH_3$ | H | $4-CF_3$ | H | H |
| Y.033 | H | $CH_3$ | $4-CF_3$ | H | H |
| Y.034 | $CH_3$ | $CH_3$ | $4-CF_3$ | H | H |
| Y.035 | $CH_2CH_3$ | $CH_3$ | $4-CF_3$ | H | H |
| Y.036 | $CH(CH_3)_2$ | $CH_3$ | $4-CF_3$ | H | H |
| Y.037 | $(CH_2)_2CH_3$ | $CH_3$ | $4-CF_3$ | H | H |
| Y.038 | $(CH_2)_3CH_3$ | $CH_3$ | $4-CF_3$ | H | H |
| Y.039 | H | $CH_2CH_3$ | $4-CF_3$ | H | H |
| Y.040 | $CH_3$ | $CH_2CH_3$ | $4-CF_3$ | H | H |
| Y.041 | $CH_2CH_3$ | $CH_2CH_3$ | $4-CF_3$ | H | H |
| Y.042 | $CH(CH_3)_2$ | $CH_2CH_3$ | $4-CF_3$ | H | H |
| Y.043 | $(CH_2)_2CH_3$ | $CH_2CH_3$ | $4-CF_3$ | H | H |
| Y.044 | $(CH_2)_3CH_3$ | $CH_2CH_3$ | $4-CF_3$ | H | H |
| Y.045 | H | $CH(CH_3)_2$ | $4-CF_3$ | H | H |
| Y.046 | $CH_3$ | $CH(CH_3)_2$ | $4-CF_3$ | H | H |
| Y.047 | $CH_2CH_3$ | $CH(CH_3)_2$ | $4-CF_3$ | H | H |
| Y.048 | $CH(CH_3)_2$ | $CH(CH_3)_2$ | $4-CF_3$ | H | H |
| Y.049 | $(CH_2)_2CH_3$ | $CH(CH_3)_2$ | $4-CF_3$ | H | H |
| Y.050 | $(CH_2)_3$ | | $4-CF_3$ | H | H |
| Y.051 | $(CH_2)_4$ | | $4-CF_3$ | H | H |
| Y.052 | $(CH_2)_5$ | | $4-CF_3$ | H | H |
| Y.053 | H | H | $4-OCF_3$ | H | H |
| Y.054 | $CH_3$ | H | $4-OCF_3$ | H | H |
| Y.055 | $CH_2CH_3$ | H | $4-OCF_3$ | H | H |
| Y.056 | $CH(CH_3)_2$ | H | $4-OCF_3$ | H | H |
| Y.057 | $(CH_2)_2CH_3$ | H | $4-OCF_3$ | H | H |
| Y.058 | $(CH_2)_3CH_3$ | H | $4-OCF_3$ | H | H |
| Y.059 | H | $CH_3$ | $4-OCF_3$ | H | H |
| Y.060 | $CH_3$ | $CH_3$ | $4-OCF_3$ | H | H |
| Y.061 | $CH_2CH_3$ | $CH_3$ | $4-OCF_3$ | H | H |
| Y.062 | $CH(CH_3)_2$ | $CH_3$ | $4-OCF_3$ | H | H |
| Y.063 | $(CH_2)_2CH_3$ | $CH_3$ | $4-OCF_3$ | H | H |
| Y.064 | $(CH_2)_3CH_3$ | $CH_3$ | $4-OCF_3$ | H | H |
| Y.065 | H | $CH_2CH_3$ | $4-OCF_3$ | H | H |
| Y.066 | $CH_3$ | $CH_2CH_3$ | $4-OCF_3$ | H | H |
| Y.067 | $CH_2CH_3$ | $CH_2CH_3$ | $4-OCF_3$ | H | H |
| Y.068 | $CH(CH_3)_2$ | $CH_2CH_3$ | $4-OCF_3$ | H | H |
| Y.069 | $(CH_2)_2CH_3$ | $CH_2CH_3$ | $4-OCF_3$ | H | H |
| Y.070 | $(CH_2)_3CH_3$ | $CH_2CH_3$ | $4-OCF_3$ | H | H |
| Y.071 | H | $CH(CH_3)_2$ | $4-OCF_3$ | H | H |
| Y.072 | $CH_3$ | $CH(CH_3)_2$ | $4-OCF_3$ | H | H |
| Y.073 | $CH_2CH_3$ | $CH(CH_3)_2$ | $4-OCF_3$ | H | H |
| Y.074 | $CH(CH_3)_2$ | $CH(CH_3)_2$ | $4-OCF_3$ | H | H |
| Y.075 | $(CH_2)_2CH_3$ | $CH(CH_3)_2$ | $4-OCF_3$ | H | H |
| Y.076 | $(CH_2)_3$ | | $4-OCF_3$ | H | H |
| Y.077 | $(CH_2)_4$ | | $4-OCF_3$ | H | H |
| Y.078 | $(CH_2)_5$ | | $4-OCF_3$ | H | H |
| Y.079 | H | $CH_3$ | 4-F | H | H |
| Y.080 | $CH_3$ | $CH_3$ | 4-F | H | H |
| Y.081 | $CH_2CH_3$ | $CH_3$ | 4-F | H | H |
| Y.082 | $CH(CH_3)_2$ | $CH_3$ | 4-F | H | H |
| Y.083 | $(CH_2)_2CH_3$ | $CH_3$ | 4-F | H | H |
| Y.084 | $(CH_2)_3CH_3$ | $CH_3$ | 4-F | H | H |
| Y.085 | H | $CH_2CH_3$ | 4-F | H | H |
| Y.086 | $CH_3$ | $CH_2CH_3$ | 4-F | H | H |
| Y.087 | $CH_2CH_3$ | $CH_2CH_3$ | 4-F | H | H |
| Y.088 | $CH(CH_3)_2$ | $CH_2CH_3$ | 4-F | H | H |
| Y.089 | $(CH_2)_2CH_3$ | $CH_2CH_3$ | 4-F | H | H |
| Y.090 | $(CH_2)_3CH_3$ | $CH_2CH_3$ | 4-F | H | H |
| Y.091 | H | H | 4-p-Cl-phenyl | H | H |
| Y.092 | $CH_3$ | H | 4-p-Cl-phenyl | H | H |
| Y.093 | $CH_2CH_3$ | H | 4-p-Cl-phenyl | H | H |
| Y.094 | $CH(CH_3)_2$ | H | 4-p-Cl-phenyl | H | H |
| Y.095 | $(CH_2)_2CH_3$ | H | 4-p-Cl-phenyl | H | H |
| Y.096 | $(CH_2)_3CH_3$ | H | 4-p-Cl-phenyl | H | H |
| Y.097 | H | $CH_3$ | 4-p-Cl-phenyl | H | H |
| Y.098 | $CH_3$ | $CH_3$ | 4-p-Cl-phenyl | H | H |
| Y.099 | $CH_2CH_3$ | $CH_3$ | 4-p-Cl-phenyl | H | H |
| Y.100 | $CH(CH_3)_2$ | $CH_3$ | 4-p-Cl-phenyl | H | H |
| Y.101 | $(CH_2)_2CH_3$ | $CH_3$ | 4-p-Cl-phenyl | H | H |
| Y.102 | $(CH_2)_3CH_3$ | $CH_3$ | 4-p-Cl-phenyl | H | H |
| Y.103 | H | $CH_2CH_3$ | 4-p-Cl-phenyl | H | H |
| Y.104 | $CH_3$ | $CH_2CH_3$ | 4-p-Cl-phenyl | H | H |
| Y.105 | $CH_2CH_3$ | $CH_2CH_3$ | 4-p-Cl-phenyl | H | H |
| Y.106 | $CH(CH_3)_2$ | $CH_2CH_3$ | 4-p-Cl-phenyl | H | H |
| Y.107 | $(CH_2)_2CH_3$ | $CH_2CH_3$ | 4-p-Cl-phenyl | H | H |
| Y.108 | $(CH_2)_3CH_3$ | $CH_2CH_3$ | 4-p-Cl-phenyl | H | H |
| Y.109 | H | $CH(CH_3)_2$ | 4-p-Cl-phenyl | H | H |
| Y.110 | $CH_3$ | $CH(CH_3)_2$ | 4-p-Cl-phenyl | H | H |
| Y.111 | $CH_2CH_3$ | $CH(CH_3)_2$ | 4-p-Cl-phenyl | H | H |
| Y.112 | $CH(CH_3)_2$ | $CH(CH_3)_2$ | 4-p-Cl-phenyl | H | H |
| Y.113 | $(CH_2)_2CH_3$ | $CH(CH_3)_2$ | 4-p-Cl-phenyl | H | H |
| Y.114 | $(CH_2)_3$ | | 4-p-Cl-phenyl | H | H |
| Y.115 | $(CH_2)_4$ | | 4-p-Cl-phenyl | H | H |
| Y.116 | $(CH_2)_5$ | | 4-p-Cl-phenyl | H | H |
| Y.117 | H | H | $4-C\equiv CC(CH_3)_3$ | H | H |
| Y.118 | $CH_3$ | H | $4-C\equiv CC(CH_3)_3$ | H | H |
| Y.119 | $CH_2CH_3$ | H | $4-C\equiv CC(CH_3)_3$ | H | H |
| Y.120 | $CH(CH_3)_2$ | H | $4-C\equiv CC(CH_3)_3$ | H | H |
| Y.121 | $(CH_2)_2CH_3$ | H | $4-C\equiv CC(CH_3)_3$ | H | H |
| Y.122 | $(CH_2)_3CH_3$ | H | $4-C\equiv CC(CH_3)_3$ | H | H |
| Y.123 | H | $CH_3$ | $4-C\equiv CC(CH_3)_3$ | H | H |
| Y.124 | $CH_3$ | $CH_3$ | $4-C\equiv CC(CH_3)_3$ | H | H |
| Y.125 | $CH_2CH_3$ | $CH_3$ | $4-C\equiv CC(CH_3)_3$ | H | H |
| Y.126 | $CH(CH_3)_2$ | $CH_3$ | $4-C\equiv CC(CH_3)_3$ | H | H |
| Y.127 | $(CH_2)_2CH_3$ | $CH_3$ | $4-C\equiv CC(CH_3)_3$ | H | H |
| Y.128 | $(CH_2)_3CH_3$ | $CH_3$ | $4-C\equiv CC(CH_3)_3$ | H | H |
| Y.129 | H | $CH_2CH_3$ | $4-C\equiv CC(CH_3)_3$ | H | H |
| Y.130 | $CH_3$ | $CH_2CH_3$ | $4-C\equiv CC(CH_3)_3$ | H | H |
| Y.131 | $CH_2CH_3$ | $CH_2CH_3$ | $4-C\equiv CC(CH_3)_3$ | H | H |
| Y.132 | $CH(CH_3)_2$ | $CH_2CH_3$ | $4-C\equiv CC(CH_3)_3$ | H | H |

TABLE Y-continued

| Comp. No. | R₁ | R₂ | R_{7a} | R_{7b} | R_{7c} |
|---|---|---|---|---|---|
| Y.133 | (CH₂)₂CH₃ | CH₂CH₃ | 4-C≡CC(CH₃)₃ | H | H |
| Y.134 | (CH₂)₃CH₃ | CH₂CH₃ | 4-C≡CC(CH₃)₃ | H | H |
| Y.135 | H | CH(CH₃)₂ | 4-C≡CC(CH₃)₃ | H | H |
| Y.136 | CH₃ | CH(CH₃)₂ | 4-C≡CC(CH₃)₃ | H | H |
| Y.137 | CH₂CH₃ | CH(CH₃)₂ | 4-C≡CC(CH₃)₃ | H | H |
| Y.138 | CH(CH₃)₂ | CH(CH₃)₂ | 4-C≡CC(CH₃)₃ | H | H |
| Y.139 | (CH₂)₂CH₃ | CH(CH₃)₂ | 4-C≡CC(CH₃)₃ | H | H |
| Y.140 | (CH₂)₃ | | 4-C≡CC(CH₃)₃ | H | H |
| Y.141 | (CH₂)₄ | | 4-C≡CC(CH₃)₃ | H | H |
| Y.142 | (CH₂)₅ | | 4-C≡CC(CH₃)₃ | H | H |
| Y.143 | H | H | 4-Cl | 2-Cl | H |
| Y.144 | CH₃ | H | 4-Cl | 2-Cl | H |
| Y.145 | CH₂CH₃ | H | 4-Cl | 2-Cl | H |
| Y.146 | CH(CH₃)₂ | H | 4-Cl | 2-Cl | H |
| Y.147 | (CH₂)₂CH₃ | H | 4-Cl | 2-Cl | H |
| Y.148 | (CH₂)₃CH₃ | H | 4-Cl | 2-Cl | H |
| Y.149 | H | CH₃ | 4-Cl | 2-Cl | H |
| Y.150 | CH₃ | CH₃ | 4-Cl | 2-Cl | H |
| Y.151 | CH₂CH₃ | CH₃ | 4-Cl | 2-Cl | H |
| Y.152 | CH(CH₃)₂ | CH₃ | 4-Cl | 2-Cl | H |
| Y.153 | (CH₂)₂CH₃ | CH₃ | 4-Cl | 2-Cl | H |
| Y.154 | (CH₂)₃CH₃ | CH₃ | 4-Cl | 2-Cl | H |
| Y.155 | H | CH₂CH₃ | 4-Cl | 2-Cl | H |
| Y.156 | CH₃ | CH₂CH₃ | 4-Cl | 2-Cl | H |
| Y.157 | CH₂CH₃ | CH₂CH₃ | 4-Cl | 2-Cl | H |
| Y.158 | CH(CH₃)₂ | CH₂CH₃ | 4-Cl | 2-Cl | H |
| Y.159 | (CH₂)₂CH₃ | CH₂CH₃ | 4-Cl | 2-Cl | H |
| Y.160 | (CH₂)₃CH₃ | CH₂CH₃ | 4-Cl | 2-Cl | H |
| Y.161 | H | CH(CH₃)₂ | 4-Cl | 2-Cl | H |
| Y.162 | CH₃ | CH(CH₃)₂ | 4-Cl | 2-Cl | H |
| Y.163 | CH₂CH₃ | CH(CH₃)₂ | 4-Cl | 2-Cl | H |
| Y.164 | CH(CH₃)₂ | CH(CH₃)₂ | 4-Cl | 2-Cl | H |
| Y.165 | (CH₂)₂CH₃ | CH(CH₃)₂ | 4-Cl | 2-Cl | H |
| Y.166 | (CH₂)₃ | | 4-Cl | 2-Cl | H |
| Y.167 | (CH₂)₄ | | 4-Cl | 2-Cl | H |
| Y.168 | (CH₂)₅ | | 4-Cl | 2-Cl | H |
| Y.169 | H | H | 4-F | 2-F | H |
| Y.170 | CH₃ | H | 4-F | 2-F | H |
| Y.171 | CH₂CH₃ | H | 4-F | 2-F | H |
| Y.172 | CH(CH₃)₂ | H | 4-F | 2-F | H |
| Y.173 | (CH₂)₂CH₃ | H | 4-F | 2-F | H |
| Y.174 | (CH₂)₃CH₃ | H | 4-F | 2-F | H |
| Y.175 | H | CH₃ | 4-F | 2-F | H |
| Y.176 | CH₃ | CH₃ | 4-F | 2-F | H |
| Y.177 | CH₂CH₃ | CH₃ | 4-F | 2-F | H |
| Y.178 | CH(CH₃)₂ | CH₃ | 4-F | 2-F | H |
| Y.179 | (CH₂)₂CH₃ | CH₃ | 4-F | 2-F | H |
| Y.180 | (CH₂)₃CH₃ | CH₃ | 4-F | 2-F | H |
| Y.181 | H | CH₂CH₃ | 4-F | 2-F | H |
| Y.182 | CH₃ | CH₂CH₃ | 4-F | 2-F | H |
| Y.183 | CH₂CH₃ | CH₂CH₃ | 4-F | 2-F | H |
| Y.184 | CH(CH₃)₂ | CH₂CH₃ | 4-F | 2-F | H |
| Y.185 | (CH₂)₂CH₃ | CH₂CH₃ | 4-F | 2-F | H |
| Y.186 | (CH₂)₃CH₃ | CH₂CH₃ | 4-F | 2-F | H |
| Y.187 | H | CH(CH₃)₂ | 4-F | 2-F | H |
| Y.188 | CH₃ | CH(CH₃)₂ | 4-F | 2-F | H |
| Y.189 | CH₂CH₃ | CH(CH₃)₂ | 4-F | 2-F | H |
| Y.190 | CH(CH₃)₂ | CH(CH₃)₂ | 4-F | 2-F | H |
| Y.191 | (CH₂)₂CH₃ | CH(CH₃)₂ | 4-F | 2-F | H |
| Y.192 | (CH₂)₃ | | 4-F | 2-F | H |
| Y.193 | (CH₂)₄ | | 4-F | 2-F | H |
| Y.194 | (CH₂)₅ | | 4-F | 2-F | H |
| Y.195 | H | H | 4-Cl | 2-F | H |
| Y.196 | CH₃ | H | 4-Cl | 2-F | H |
| Y.197 | CH₂CH₃ | H | 4-Cl | 2-F | H |
| Y.198 | CH(CH₃)₂ | H | 4-Cl | 2-F | H |
| Y.199 | (CH₂)₂CH₃ | H | 4-Cl | 2-F | H |
| Y.200 | (CH₂)₃CH₃ | H | 4-Cl | 2-F | H |
| Y.201 | H | CH₃ | 4-Cl | 2-F | H |
| Y.202 | CH₃ | CH₃ | 4-Cl | 2-F | H |
| Y.203 | CH₂CH₃ | CH₃ | 4-Cl | 2-F | H |
| Y.204 | CH(CH₃)₂ | CH₃ | 4-Cl | 2-F | H |
| Y.205 | (CH₂)₂CH₃ | CH₃ | 4-Cl | 2-F | H |
| Y.206 | (CH₂)₃CH₃ | CH₃ | 4-Cl | 2-F | H |
| Y.207 | H | CH₂CH₃ | 4-Cl | 2-F | H |
| Y.208 | CH₃ | CH₂CH₃ | 4-Cl | 2-F | H |
| Y.209 | CH₂CH₃ | CH₂CH₃ | 4-Cl | 2-F | H |
| Y.210 | CH(CH₃)₂ | CH₂CH₃ | 4-Cl | 2-F | H |
| Y.211 | (CH₂)₂CH₃ | CH₂CH₃ | 4-Cl | 2-F | H |
| Y.212 | (CH₂)₃CH₃ | CH₂CH₃ | 4-Cl | 2-F | H |
| Y.213 | H | CH(CH₃)₂ | 4-Cl | 2-F | H |
| Y.214 | CH₃ | CH(CH₃)₂ | 4-Cl | 2-F | H |
| Y.215 | CH₂CH₃ | CH(CH₃)₂ | 4-Cl | 2-F | H |
| Y.216 | CH(CH₃)₂ | CH(CH₃)₂ | 4-Cl | 2-F | H |
| Y.217 | (CH₂)₂CH₃ | CH(CH₃)₂ | 4-Cl | 2-F | H |
| Y.218 | (CH₂)₃ | | 4-Cl | 2-F | H |
| Y.219 | (CH₂)₄ | | 4-Cl | 2-F | H |
| Y.220 | (CH₂)₅ | | 4-Cl | 2-F | H |
| Y.221 | H | H | 2-Cl | 4-F | H |
| Y.222 | CH₃ | H | 2-Cl | 4-F | H |
| Y.223 | CH₂CH₃ | H | 2-Cl | 4-F | H |
| Y.224 | CH(CH₃)₂ | H | 2-Cl | 4-F | H |
| Y.225 | (CH₂)₂CH₃ | H | 2-Cl | 4-F | H |
| Y.226 | (CH₂)₃CH₃ | H | 2-Cl | 4-F | H |
| Y.227 | H | CH₃ | 2-Cl | 4-F | H |
| Y.228 | CH₃ | CH₃ | 2-Cl | 4-F | H |
| Y.229 | CH₂CH₃ | CH₃ | 2-Cl | 4-F | H |
| Y.230 | CH(CH₃)₂ | CH₃ | 2-Cl | 4-F | H |
| Y.231 | (CH₂)₂CH₃ | CH₃ | 2-Cl | 4-F | H |
| Y.232 | (CH₂)₃CH₃ | CH₃ | 2-Cl | 4-F | H |
| Y.233 | H | CH₂CH₃ | 2-Cl | 4-F | H |
| Y.234 | CH₃ | CH₂CH₃ | 2-Cl | 4-F | H |
| Y.235 | CH₂CH₃ | CH₂CH₃ | 2-Cl | 4-F | H |
| Y.236 | CH(CH₃)₂ | CH₂CH₃ | 2-Cl | 4-F | H |
| Y.237 | (CH₂)₂CH₃ | CH₂CH₃ | 2-Cl | 4-F | H |
| Y.238 | (CH₂)₃CH₃ | CH₂CH₃ | 2-Cl | 4-F | H |
| Y.239 | H | CH(CH₃)₂ | 2-Cl | 4-F | H |
| Y.240 | CH₃ | CH(CH₃)₂ | 2-Cl | 4-F | H |
| Y.241 | CH₂CH₃ | CH(CH₃)₂ | 2-Cl | 4-F | H |
| Y.242 | CH(CH₃)₂ | CH(CH₃)₂ | 2-Cl | 4-F | H |
| Y.243 | (CH₂)₂CH₃ | CH(CH₃)₂ | 2-Cl | 4-F | H |
| Y.244 | (CH₂)₃ | | 2-Cl | 4-F | H |
| Y.245 | (CH₂)₄ | | 2-Cl | 4-F | H |
| Y.246 | (CH₂)₅ | | 2-Cl | 4-F | H |
| Y.247 | H | H | 4-p-Cl-phenyl | 2-Cl | H |
| Y.248 | CH₃ | H | 4-p-Cl-phenyl | 2-Cl | H |
| Y.249 | CH₂CH₃ | H | 4-p-Cl-phenyl | 2-Cl | H |
| Y.250 | CH(CH₃)₂ | H | 4-p-Cl-phenyl | 2-Cl | H |
| Y.251 | (CH₂)₂CH₃ | H | 4-p-Cl-phenyl | 2-Cl | H |
| Y.252 | H | CH₃ | 4-p-Cl-phenyl | 2-Cl | H |
| Y.253 | CH₃ | CH₃ | 4-p-Cl-phenyl | 2-Cl | H |
| Y.254 | CH₂CH₃ | CH₃ | 4-p-Cl-phenyl | 2-Cl | H |
| Y.255 | CH(CH₃)₂ | CH₃ | 4-p-Cl-phenyl | 2-Cl | H |
| Y.256 | (CH₂)₂CH₃ | CH₃ | 4-p-Cl-phenyl | 2-Cl | H |
| Y.257 | H | H | 2-Cl | 4-Cl | 6-Cl |
| Y.258 | CH₃ | H | 2-Cl | 4-Cl | 6-Cl |
| Y.259 | CH₂CH₃ | H | 2-Cl | 4-Cl | 6-Cl |
| Y.260 | CH(CH₃)₂ | H | 2-Cl | 4-Cl | 6-Cl |
| Y.261 | (CH₂)₂CH₃ | H | 2-Cl | 4-Cl | 6-Cl |
| Y.262 | (CH₂)₃CH₃ | H | 2-Cl | 4-Cl | 6-Cl |
| Y.263 | H | CH₃ | 2-Cl | 4-Cl | 6-Cl |
| Y.264 | CH₃ | CH₃ | 2-Cl | 4-Cl | 6-Cl |
| Y.265 | CH₂CH₃ | CH₃ | 2-Cl | 4-Cl | 6-Cl |
| Y.266 | CH(CH₃)₂ | CH₃ | 2-Cl | 4-Cl | 6-Cl |
| Y.267 | (CH₂)₂CH₃ | CH₃ | 2-Cl | 4-Cl | 6-Cl |
| Y.268 | (CH₂)₃CH₃ | CH₃ | 2-Cl | 4-Cl | 6-Cl |
| Y.269 | H | CH₂CH₃ | 2-Cl | 4-Cl | 6-Cl |
| Y.270 | CH₃ | CH₂CH₃ | 2-Cl | 4-Cl | 6-Cl |
| Y.271 | CH₂CH₃ | CH₂CH₃ | 2-Cl | 4-Cl | 6-Cl |
| Y.272 | CH(CH₃)₂ | CH₂CH₃ | 2-Cl | 4-Cl | 6-Cl |
| Y.273 | (CH₂)₂CH₃ | CH₂CH₃ | 2-Cl | 4-Cl | 6-Cl |
| Y.274 | (CH₂)₃CH₃ | CH₂CH₃ | 2-Cl | 4-Cl | 6-Cl |
| Y.275 | H | CH(CH₃)₂ | 2-Cl | 4-Cl | 6-Cl |
| Y.276 | CH₃ | CH(CH₃)₂ | 2-Cl | 4-Cl | 6-Cl |
| Y.277 | CH₂CH₃ | CH(CH₃)₂ | 2-Cl | 4-Cl | 6-Cl |
| Y.278 | CH(CH₃)₂ | CH(CH₃)₂ | 2-Cl | 4-Cl | 6-Cl |
| Y.279 | (CH₂)₂CH₃ | CH(CH₃)₂ | 2-Cl | 4-Cl | 6-Cl |
| Y.280 | (CH₂)₃ | | 2-Cl | 4-Cl | 6-Cl |
| Y.281 | (CH₂)₄ | | 2-Cl | 4-Cl | 6-Cl |
| Y.282 | (CH₂)₅ | | 2-Cl | 4-Cl | 6-Cl |

Table 1 provides 282 compounds of formula (IA), wherein A is

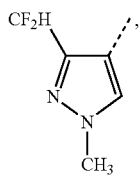

wherein the broken lines indicate the point of attachment of the group A to the amide group, and $R_1$, $R_2$, $R_{7a}$, $R_{7b}$ and $R_{7c}$ are as defined in Table Y. For example, compound 1.001 occurs in Z- and E-from or in mixtures thereof. Compound 1.001 (Z-form) and compound 1.001 (E-form) have the following structure:

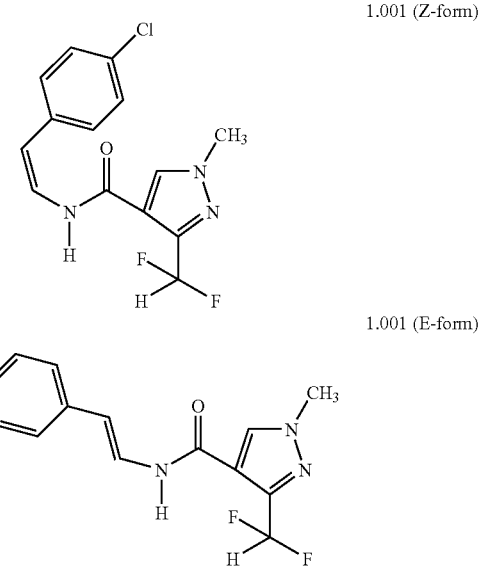

1.001 (Z-form)

1.001 (E-form)

Table 2 provides 282 compounds of formula (IA) wherein A is

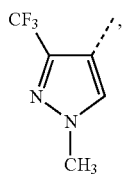

wherein the broken lines indicate the point of attachment of the group A to the amide group, and $R_1$, $R_2$, $R_{7a}$, $R_{7b}$ and $R_{7c}$ are as defined in Table Y.

Table 3 provides 282 compounds of formula (IA) wherein A is

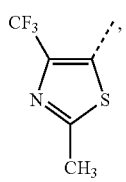

wherein the broken lines indicate the point of attachment of the group A to the amide group, and $R_1$, $R_2$, $R_{7a}$, $R_{7b}$ and $R_{7c}$ are as defined in Table Y.

Table 4 provides 282 compounds of formula (IA) wherein A is

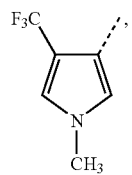

wherein the broken lines indicate the point of attachment of the group A to the amide group, and $R_1$, $R_2$, $R_{7a}$, $R_{7b}$ and $R_{7c}$ are as defined in Table Y.

Table 5 provides 282 compounds of formula (IA) wherein A is

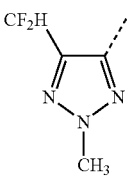

wherein the broken lines indicate the point of attachment of the group A to the amide group, and $R_1$, $R_2$, $R_{7a}$, $R_{7b}$ and $R_{7c}$ are as defined in Table Y.

Table 6 provides 282 compounds of formula (IA) wherein A is

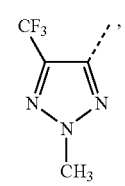

wherein the broken lines indicate the point of attachment of the group A to the amide group, and $R_1$, $R_2$, $R_{7a}$, $R_{7b}$ and $R_{7c}$ are as defined in Table Y.

Tables 7 to 12: Compounds of Formula ID

The invention is further illustrated by the preferred individual compounds of formula ID listed below in Tables 7 to 12. Characterising data is given in Table 13.

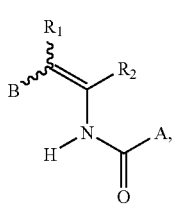

(ID)

Each of Tables 7 to 12, which follow the Table W below, comprises 288 compounds of the formula ID in which B, $R_1$ and $R_2$ have the values given in Table W and A has the value given in the relevant Table 7 to 12. Thus Table 7 corresponds to Table W when W is 7 and A has the value given under the Table 7 heading, Table 8 corresponds to Table W when W is 8 and A has the value given under the Table 8 heading, and so on for Tables 9 to 12. As it is described for compounds of formula IC, also each compound of formula ID occurs in different isomeric forms.

TABLE W

In Table W the group B stands for the group $B_1$, $B_2$, $B_3$ or $B_4$:

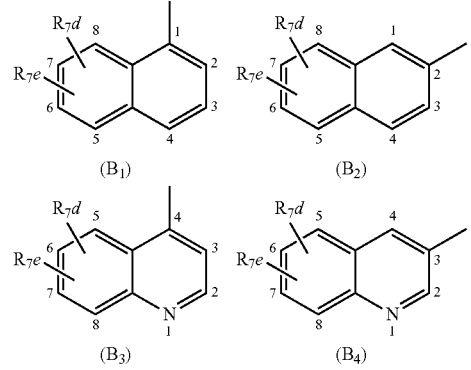

(B₁)  (B₂)  (B₃)  (B₄)

| Compound No. | B | $R_1$ | $R_2$ | $R_{7d}$ | $R_{7e}$ |
|---|---|---|---|---|---|
| W.001 | B₁ | H | H | 2-Cl | H |
| W.002 | B₁ | H | CH₃ | 2-Cl | H |
| W.003 | B₁ | H | CH₂CH₃ | 2-Cl | H |
| W.004 | B₁ | H | (CH₂)₂CH₃ | 2-Cl | H |
| W.005 | B₁ | H | CH(CH₃)₂ | 2-Cl | H |
| W.006 | B₁ | CH₃ | CH₃ | 2-Cl | H |
| W.007 | B₁ | CH₃ | CH₂CH₃ | 2-Cl | H |
| W.008 | B₁ | CH₃ | (CH₂)₂CH₃ | 2-Cl | H |
| W.009 | B₁ | CH₃ | CH(CH₃)₂ | 2-Cl | H |
| W.010 | B₁ | H | H | 4-Cl | H |
| W.011 | B₁ | H | CH₃ | 4-Cl | H |
| W.012 | B₁ | H | CH₂CH₃ | 4-Cl | H |
| W.013 | B₁ | H | (CH₂)₂CH₃ | 4-Cl | H |
| W.014 | B₁ | H | CH(CH₃)₂ | 4-Cl | H |
| W.015 | B₁ | CH₃ | CH₃ | 4-Cl | H |
| W.016 | B₁ | CH₃ | CH₂CH₃ | 4-Cl | H |
| W.017 | B₁ | CH₃ | (CH₂)₂CH₃ | 4-Cl | H |
| W.018 | B₁ | CH₃ | CH(CH₃)₂ | 4-Cl | H |
| W.019 | B₁ | H | H | 5-Cl | H |
| W.020 | B₁ | H | CH₃ | 5-Cl | H |
| W.021 | B₁ | H | CH₂CH₃ | 5-Cl | H |
| W.022 | B₁ | H | (CH₂)₂CH₃ | 5-Cl | H |
| W.023 | B₁ | H | CH(CH₃)₂ | 5-Cl | H |
| W.024 | B₁ | CH₃ | CH₃ | 5-Cl | H |
| W.025 | B₁ | CH₃ | CH₂CH₃ | 5-Cl | H |
| W.026 | B₁ | CH₃ | (CH₂)₂CH₃ | 5-Cl | H |
| W.027 | B₁ | CH₃ | CH(CH₃)₂ | 5-Cl | H |
| W.028 | B₁ | H | H | 6-Cl | H |
| W.029 | B₁ | H | CH₃ | 6-Cl | H |
| W.030 | B₁ | H | CH₂CH₃ | 6-Cl | H |
| W.031 | B₁ | H | (CH₂)₂CH₃ | 6-Cl | H |
| W.032 | B₁ | H | CH(CH₃)₂ | 6-Cl | H |
| W.033 | B₁ | CH₃ | CH₃ | 6-Cl | H |
| W.034 | B₁ | CH₃ | CH₂CH₃ | 6-Cl | H |
| W.035 | B₁ | CH₃ | (CH₂)₂CH₃ | 6-Cl | H |
| W.036 | B₁ | CH₃ | CH(CH₃)₂ | 6-Cl | H |
| W.037 | B₁ | H | H | 8-Cl | H |
| W.038 | B₁ | H | CH₃ | 8-Cl | H |
| W.039 | B₁ | H | CH₂CH₃ | 8-Cl | H |
| W.040 | B₁ | H | (CH₂)₂CH₃ | 8-Cl | H |
| W.041 | B₁ | H | CH(CH₃)₂ | 8-Cl | H |
| W.042 | B₁ | CH₃ | CH₃ | 8-Cl | H |
| W.043 | B₁ | CH₃ | CH₂CH₃ | 8-Cl | H |
| W.044 | B₁ | CH₃ | (CH₂)₂CH₃ | 8-Cl | H |
| W.045 | B₁ | CH₃ | CH(CH₃)₂ | 8-Cl | H |
| W.046 | B₁ | H | H | 4-p-Cl-phenyl | H |
| W.047 | B₁ | H | CH₃ | 4-p-Cl-phenyl | H |
| W.048 | B₁ | H | CH₂CH₃ | 4-p-Cl-phenyl | H |
| W.049 | B₁ | H | (CH₂)₂CH₃ | 4-p-Cl-phenyl | H |
| W.050 | B₁ | H | CH(CH₃)₂ | 4-p-Cl-phenyl | H |
| W.051 | B₁ | CH₃ | CH₃ | 4-p-Cl-phenyl | H |
| W.052 | B₁ | CH₃ | CH₂CH₃ | 4-p-Cl-phenyl | H |
| W.053 | B₁ | CH₃ | (CH₂)₂CH₃ | 4-p-Cl-phenyl | H |
| W.054 | B₁ | CH₃ | CH(CH₃)₂ | 4-p-Cl-phenyl | H |
| W.055 | B₁ | H | H | 8-p-Cl-phenyl | H |
| W.056 | B₁ | H | CH₃ | 8-p-Cl-phenyl | H |
| W.057 | B₁ | H | CH₂CH₃ | 8-p-Cl-phenyl | H |
| W.058 | B₁ | H | (CH₂)₂CH₃ | 8-p-Cl-phenyl | H |
| W.059 | B₁ | H | CH(CH₃)₂ | 8-p-Cl-phenyl | H |
| W.060 | B₁ | CH₃ | CH₃ | 8-p-Cl-phenyl | H |
| W.061 | B₁ | CH₃ | CH₂CH₃ | 8-p-Cl-phenyl | H |
| W.062 | B₁ | CH₃ | (CH₂)₂CH₃ | 8-p-Cl-phenyl | H |
| W.063 | B₁ | CH₃ | CH(CH₃)₂ | 8-p-Cl-phenyl | H |
| W.064 | B₁ | H | H | 2-Cl | 4-Cl |
| W.065 | B₁ | H | CH₃ | 2-Cl | 4-Cl |
| W.066 | B₁ | H | CH₂CH₃ | 2-Cl | 4-Cl |
| W.067 | B₁ | H | (CH₂)₂CH₃ | 2-Cl | 4-Cl |
| W.068 | B₁ | H | CH(CH₃)₂ | 2-Cl | 4-Cl |
| W.069 | B₁ | CH₃ | CH₃ | 2-Cl | 4-Cl |
| W.070 | B₁ | CH₃ | CH₂CH₃ | 2-Cl | 4-Cl |
| W.071 | B₁ | CH₃ | (CH₂)₂CH₃ | 2-Cl | 4-Cl |
| W.072 | B₁ | CH₃ | CH(CH₃)₂ | 2-Cl | 4-Cl |
| W.073 | B₁ | H | H | 4-p-Cl-phenyl | 2-Cl |
| W.074 | B₁ | H | CH₃ | 4-p-Cl-phenyl | 2-Cl |
| W.075 | B₁ | H | CH₂CH₃ | 4-p-Cl-phenyl | 2-Cl |
| W.076 | B₁ | H | (CH₂)₂CH₃ | 4-p-Cl-phenyl | 2-Cl |
| W.077 | B₁ | H | CH(CH₃)₂ | 4-p-Cl-phenyl | 2-Cl |
| W.078 | B₁ | CH₃ | CH₃ | 4-p-Cl-phenyl | 2-Cl |
| W.079 | B₁ | CH₃ | CH₂CH₃ | 4-p-Cl-phenyl | 2-Cl |
| W.080 | B₁ | CH₃ | (CH₂)₂CH₃ | 4-p-Cl-phenyl | 2-Cl |
| W.081 | B₁ | CH₃ | CH(CH₃)₂ | 4-p-Cl-phenyl | 2-Cl |
| W.082 | B₂ | H | H | 6-Cl | H |
| W.083 | B₂ | H | CH₃ | 6-Cl | H |
| W.084 | B₂ | H | CH₂CH₃ | 6-Cl | H |
| W.085 | B₂ | H | (CH₂)₂CH₃ | 6-Cl | H |
| W.086 | B₂ | H | CH(CH₃)₂ | 6-Cl | H |
| W.087 | B₂ | CH₃ | CH₃ | 6-Cl | H |
| W.088 | B₂ | CH₃ | CH₂CH₃ | 6-Cl | H |
| W.089 | B₂ | CH₃ | (CH₂)₂CH₃ | 6-Cl | H |
| W.090 | B₂ | CH₃ | CH(CH₃)₂ | 6-Cl | H |
| W.091 | B₂ | H | H | 6-CF₃ | H |
| W.092 | B₂ | H | CH₃ | 6-CF₃ | H |
| W.093 | B₂ | H | CH₂CH₃ | 6-CF₃ | H |
| W.094 | B₂ | H | (CH₂)₂CH₃ | 6-CF₃ | H |
| W.095 | B₂ | H | CH(CH₃)₂ | 6-CF₃ | H |
| W.096 | B₂ | CH₃ | CH₃ | 6-CF₃ | H |
| W.097 | B₂ | CH₃ | CH₂CH₃ | 6-CF₃ | H |
| W.098 | B₂ | CH₃ | (CH₂)₂CH₃ | 6-CF₃ | H |
| W.099 | B₂ | CH₃ | CH(CH₃)₂ | 6-CF₃ | H |
| W.100 | B₂ | H | H | 6-OCF₃ | H |
| W.101 | B₂ | H | CH₃ | 6-OCF₃ | H |

TABLE W-continued

In Table W the group B stands for the group $B_1$, $B_2$, $B_3$ or $B_4$:

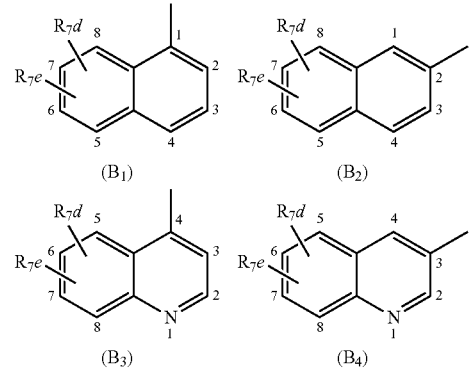

(B$_1$)  (B$_2$)  (B$_3$)  (B$_4$)

| Compound No. | B | $R_1$ | $R_2$ | $R_{7d}$ | $R_{7e}$ |
|---|---|---|---|---|---|
| W.102 | B$_2$ | H | CH$_2$CH$_3$ | 6-OCF$_3$ | H |
| W.103 | B$_2$ | H | (CH$_2$)$_2$CH$_3$ | 6-OCF$_3$ | H |
| W.104 | B$_2$ | H | CH(CH$_3$)$_2$ | 6-OCF$_3$ | H |
| W.105 | B$_2$ | CH$_3$ | CH$_3$ | 6-OCF$_3$ | H |
| W.106 | B$_2$ | CH$_3$ | CH$_2$CH$_3$ | 6-OCF$_3$ | H |
| W.107 | B$_2$ | CH$_3$ | (CH$_2$)$_2$CH$_3$ | 6-OCF$_3$ | H |
| W.108 | B$_2$ | CH$_3$ | CH(CH$_3$)$_2$ | 6-OCF$_3$ | H |
| W.109 | B$_2$ | H | H | 6-p-Cl-phenyl | H |
| W.110 | B$_2$ | H | CH$_3$ | 6-p-Cl-phenyl | H |
| W.111 | B$_2$ | H | CH$_2$CH$_3$ | 6-p-Cl-phenyl | H |
| W.112 | B$_2$ | H | (CH$_2$)$_2$CH$_3$ | 6-p-Cl-phenyl | H |
| W.113 | B$_2$ | H | CH(CH$_3$)$_2$ | 6-p-Cl-phenyl | H |
| W.114 | B$_2$ | CH$_3$ | CH$_3$ | 6-p-Cl-phenyl | H |
| W.115 | B$_2$ | CH$_3$ | CH$_2$CH$_3$ | 6-p-Cl-phenyl | H |
| W.116 | B$_2$ | CH$_3$ | (CH$_2$)$_2$CH$_3$ | 6-p-Cl-phenyl | H |
| W.117 | B$_2$ | CH$_3$ | CH(CH$_3$)$_2$ | 6-p-Cl-phenyl | H |
| W.118 | B$_3$ | H | H | 2-Cl | H |
| W.119 | B$_3$ | H | CH$_3$ | 2-Cl | H |
| W.120 | B$_3$ | H | CH$_2$CH$_3$ | 2-Cl | H |
| W.121 | B$_3$ | H | (CH$_2$)$_2$CH$_3$ | 2-Cl | H |
| W.122 | B$_3$ | H | CH(CH$_3$)$_2$ | 2-Cl | H |
| W.123 | B$_3$ | CH$_3$ | CH$_3$ | 2-Cl | H |
| W.124 | B$_3$ | CH$_3$ | CH$_2$CH$_3$ | 2-Cl | H |
| W.125 | B$_3$ | CH$_3$ | (CH$_2$)$_2$CH$_3$ | 2-Cl | H |
| W.126 | B$_3$ | CH$_3$ | CH(CH$_3$)$_2$ | 2-Cl | H |
| W.127 | B$_3$ | H | H | 3-Cl | H |
| W.128 | B$_3$ | H | CH$_3$ | 3-Cl | H |
| W.129 | B$_3$ | H | CH$_2$CH$_3$ | 3-Cl | H |
| W.130 | B$_3$ | H | (CH$_2$)$_2$CH$_3$ | 3-Cl | H |
| W.131 | B$_3$ | H | CH(CH$_3$)$_2$ | 3-Cl | H |
| W.132 | B$_3$ | CH$_3$ | CH$_3$ | 3-Cl | H |
| W.133 | B$_3$ | CH$_3$ | CH$_2$CH$_3$ | 3-Cl | H |
| W.134 | B$_3$ | CH$_3$ | (CH$_2$)$_2$CH$_3$ | 3-Cl | H |
| W.135 | B$_3$ | CH$_3$ | CH(CH$_3$)$_2$ | 3-Cl | H |
| W.136 | B$_3$ | H | H | 5-Cl | H |
| W.137 | B$_3$ | H | CH$_3$ | 5-Cl | H |
| W.138 | B$_3$ | H | CH$_2$CH$_3$ | 5-Cl | H |
| W.139 | B$_3$ | H | (CH$_2$)$_2$CH$_3$ | 5-Cl | H |
| W.140 | B$_3$ | H | CH(CH$_3$)$_2$ | 5-Cl | H |
| W.141 | B$_3$ | CH$_3$ | CH$_3$ | 5-Cl | H |
| W.142 | B$_3$ | CH$_3$ | CH$_2$CH$_3$ | 5-Cl | H |
| W.143 | B$_3$ | CH$_3$ | (CH$_2$)$_2$CH$_3$ | 5-Cl | H |
| W.144 | B$_3$ | CH$_3$ | CH(CH$_3$)$_2$ | 5-Cl | H |
| W.145 | B$_3$ | H | H | 6-Cl | H |
| W.146 | B$_3$ | H | CH$_3$ | 6-Cl | H |
| W.147 | B$_3$ | H | CH$_2$CH$_3$ | 6-Cl | H |
| W.148 | B$_3$ | H | (CH$_2$)$_2$CH$_3$ | 6-Cl | H |
| W.149 | B$_3$ | H | CH(CH$_3$)$_2$ | 6-Cl | H |
| W.150 | B$_3$ | CH$_3$ | CH$_3$ | 6-Cl | H |
| W.151 | B$_3$ | CH$_3$ | CH$_2$CH$_3$ | 6-Cl | H |
| W.152 | B$_3$ | CH$_3$ | (CH$_2$)$_2$CH$_3$ | 6-Cl | H |
| W.153 | B$_3$ | CH$_3$ | CH(CH$_3$)$_2$ | 6-Cl | H |
| W.154 | B$_3$ | H | H | 8-Cl | H |
| W.155 | B$_3$ | H | CH$_3$ | 8-Cl | H |
| W.156 | B$_3$ | H | CH$_2$CH$_3$ | 8-Cl | H |
| W.157 | B$_3$ | H | (CH$_2$)$_2$CH$_3$ | 8-Cl | H |
| W.158 | B$_3$ | H | CH(CH$_3$)$_2$ | 8-Cl | H |
| W.159 | B$_3$ | CH$_3$ | CH$_3$ | 8-Cl | H |
| W.160 | B$_3$ | CH$_3$ | CH$_2$CH$_3$ | 8-Cl | H |
| W.161 | B$_3$ | CH$_3$ | (CH$_2$)$_2$CH$_3$ | 8-Cl | H |
| W.162 | B$_3$ | CH$_3$ | CH(CH$_3$)$_2$ | 8-Cl | H |
| W.163 | B$_3$ | H | H | 2-Cl | 5-Cl |
| W.164 | B$_3$ | H | CH$_3$ | 2-Cl | 5-Cl |
| W.165 | B$_3$ | H | CH$_2$CH$_3$ | 2-Cl | 5-Cl |
| W.166 | B$_3$ | H | (CH$_2$)$_2$CH$_3$ | 2-Cl | 5-Cl |
| W.167 | B$_3$ | H | CH(CH$_3$)$_2$ | 2-Cl | 5-Cl |
| W.168 | B$_3$ | CH$_3$ | CH$_3$ | 2-Cl | 5-Cl |
| W.169 | B$_3$ | CH$_3$ | CH$_2$CH$_3$ | 2-Cl | 5-Cl |
| W.170 | B$_3$ | CH$_3$ | (CH$_2$)$_2$CH$_3$ | 2-Cl | 5-Cl |
| W.171 | B$_3$ | CH$_3$ | CH(CH$_3$)$_2$ | 2-Cl | 5-Cl |
| W.172 | B$_3$ | H | H | 2-Cl | 6-Cl |
| W.173 | B$_3$ | H | CH$_3$ | 2-Cl | 6-Cl |
| W.174 | B$_3$ | H | CH$_2$CH$_3$ | 2-Cl | 6-Cl |
| W.175 | B$_3$ | H | (CH$_2$)$_2$CH$_3$ | 2-Cl | 6-Cl |
| W.176 | B$_3$ | H | CH(CH$_3$)$_2$ | 2-Cl | 6-Cl |
| W.177 | B$_3$ | CH$_3$ | CH$_3$ | 2-Cl | 6-Cl |
| W.178 | B$_3$ | CH$_3$ | CH$_2$CH$_3$ | 2-Cl | 6-Cl |
| W.179 | B$_3$ | CH$_3$ | (CH$_2$)$_2$CH$_3$ | 2-Cl | 6-Cl |
| W.180 | B$_3$ | CH$_3$ | CH(CH$_3$)$_2$ | 2-Cl | 6-Cl |
| W.181 | B$_3$ | H | H | 2-Cl | 8-Cl |
| W.182 | B$_3$ | H | CH$_3$ | 2-Cl | 8-Cl |
| W.183 | B$_3$ | H | CH$_2$CH$_3$ | 2-Cl | 8-Cl |
| W.184 | B$_3$ | H | (CH$_2$)$_2$CH$_3$ | 2-Cl | 8-Cl |
| W.185 | B$_3$ | H | CH(CH$_3$)$_2$ | 2-Cl | 8-Cl |
| W.186 | B$_3$ | CH$_3$ | CH$_3$ | 2-Cl | 8-Cl |
| W.187 | B$_3$ | CH$_3$ | CH$_2$CH$_3$ | 2-Cl | 8-Cl |
| W.188 | B$_3$ | CH$_3$ | (CH$_2$)$_2$CH$_3$ | 2-Cl | 8-Cl |
| W.189 | B$_3$ | CH$_3$ | CH(CH$_3$)$_2$ | 2-Cl | 8-Cl |
| W.190 | B$_3$ | H | H | 6-p-Cl-phenyl | 2-Cl |
| W.191 | B$_3$ | H | CH$_3$ | 6-p-Cl-phenyl | 2-Cl |
| W.192 | B$_3$ | H | CH$_2$CH$_3$ | 6-p-Cl-phenyl | 2-Cl |
| W.193 | B$_3$ | H | (CH$_2$)$_2$CH$_3$ | 6-p-Cl-phenyl | 2-Cl |
| W.194 | B$_3$ | H | CH(CH$_3$)$_2$ | 6-p-Cl-phenyl | 2-Cl |
| W.195 | B$_3$ | CH$_3$ | CH$_3$ | 6-p-Cl-phenyl | 2-Cl |
| W.196 | B$_3$ | CH$_3$ | CH$_2$CH$_3$ | 6-p-Cl-phenyl | 2-Cl |
| W.197 | B$_3$ | CH$_3$ | (CH$_2$)$_2$CH$_3$ | 6-p-Cl-phenyl | 2-Cl |
| W.198 | B$_3$ | CH$_3$ | CH(CH$_3$)$_2$ | 6-p-Cl-phenyl | 2-Cl |
| W.199 | B$_4$ | H | H | 2-Cl | H |
| W.200 | B$_4$ | H | CH$_3$ | 2-Cl | H |
| W.201 | B$_4$ | H | CH$_2$CH$_3$ | 2-Cl | H |
| W.202 | B$_4$ | H | (CH$_2$)$_2$CH$_3$ | 2-Cl | H |
| W.203 | B$_4$ | H | CH(CH$_3$)$_2$ | 2-Cl | H |
| W.204 | B$_4$ | CH$_3$ | CH$_3$ | 2-Cl | H |
| W.205 | B$_4$ | CH$_3$ | CH$_2$CH$_3$ | 2-Cl | H |
| W.206 | B$_4$ | CH$_3$ | (CH$_2$)$_2$CH$_3$ | 2-Cl | H |
| W.207 | B$_4$ | CH$_3$ | CH(CH$_3$)$_2$ | 2-Cl | H |
| W.208 | B$_4$ | H | H | 4-Cl | H |
| W.209 | B$_4$ | H | CH$_3$ | 4-Cl | H |
| W.210 | B$_4$ | H | CH$_2$CH$_3$ | 4-Cl | H |
| W.211 | B$_4$ | H | (CH$_2$)$_2$CH$_3$ | 4-Cl | H |
| W.212 | B$_4$ | H | CH(CH$_3$)$_2$ | 4-Cl | H |
| W.213 | B$_4$ | CH$_3$ | CH$_3$ | 4-Cl | H |

TABLE W-continued

In Table W the group B stands for the group $B_1$, $B_2$, $B_3$ or $B_4$:

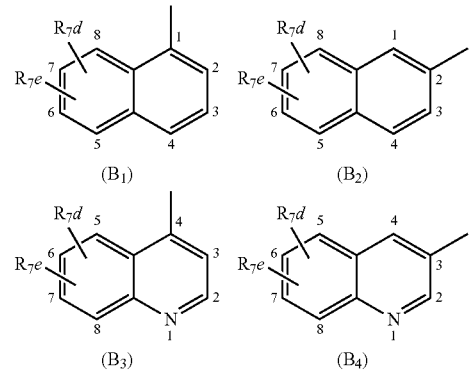

(B₁)  (B₂)

(B₃)  (B₄)

| Compound No. | B | $R_1$ | $R_2$ | $R_{7d}$ | $R_{7e}$ |
|---|---|---|---|---|---|
| W.214 | $B_4$ | $CH_3$ | $CH_2CH_3$ | 4-Cl | H |
| W.215 | $B_4$ | $CH_3$ | $(CH_2)_2CH_3$ | 4-Cl | H |
| W.216 | $B_4$ | $CH_3$ | $CH(CH_3)_2$ | 4-Cl | H |
| W.217 | $B_4$ | H | H | 5-Cl | H |
| W.218 | $B_4$ | H | $CH_3$ | 5-Cl | H |
| W.219 | $B_4$ | H | $CH_2CH_3$ | 5-Cl | H |
| W.220 | $B_4$ | H | $(CH_2)_2CH_3$ | 5-Cl | H |
| W.221 | $B_4$ | H | $CH(CH_3)_2$ | 5-Cl | H |
| W.222 | $B_4$ | $CH_3$ | $CH_3$ | 5-Cl | H |
| W.223 | $B_4$ | $CH_3$ | $CH_2CH_3$ | 5-Cl | H |
| W.224 | $B_4$ | $CH_3$ | $(CH_2)_2CH_3$ | 5-Cl | H |
| W.225 | $B_4$ | $CH_3$ | $CH(CH_3)_2$ | 5-Cl | H |
| W.226 | $B_4$ | H | H | 7-Cl | H |
| W.227 | $B_4$ | H | $CH_3$ | 7-Cl | H |
| W.228 | $B_4$ | H | $CH_2CH_3$ | 7-Cl | H |
| W.229 | $B_4$ | H | $(CH_2)_2CH_3$ | 7-Cl | H |
| W.230 | $B_4$ | H | $CH(CH_3)_2$ | 7-Cl | H |
| W.231 | $B_4$ | $CH_3$ | $CH_3$ | 7-Cl | H |
| W.232 | $B_4$ | $CH_3$ | $CH_2CH_3$ | 7-Cl | H |
| W.233 | $B_4$ | $CH_3$ | $(CH_2)_2CH_3$ | 7-Cl | H |
| W.234 | $B_4$ | $CH_3$ | $CH(CH_3)_2$ | 7-Cl | H |
| W.235 | $B_4$ | H | H | 8-Cl | H |
| W.236 | $B_4$ | H | $CH_3$ | 8-Cl | H |
| W.237 | $B_4$ | H | $CH_2CH_3$ | 8-Cl | H |
| W.238 | $B_4$ | H | $(CH_2)_2CH_3$ | 8-Cl | H |
| W.239 | $B_4$ | H | $CH(CH_3)_2$ | 8-Cl | H |
| W.240 | $B_4$ | $CH_3$ | $CH_3$ | 8-Cl | H |
| W.241 | $B_4$ | $CH_3$ | $CH_2CH_3$ | 8-Cl | H |
| W.242 | $B_4$ | $CH_3$ | $(CH_2)_2CH_3$ | 8-Cl | H |
| W.243 | $B_4$ | $CH_3$ | $CH(CH_3)_2$ | 8-Cl | H |
| W.244 | $B_4$ | H | H | 2-Cl | 4-Cl |
| W.245 | $B_4$ | H | $CH_3$ | 2-Cl | 4-Cl |
| W.246 | $B_4$ | H | $CH_2CH_3$ | 2-Cl | 4-Cl |
| W.247 | $B_4$ | H | $(CH_2)_2CH_3$ | 2-Cl | 4-Cl |
| W.248 | $B_4$ | H | $CH(CH_3)_2$ | 2-Cl | 4-Cl |
| W.249 | $B_4$ | $CH_3$ | $CH_3$ | 2-Cl | 4-Cl |
| W.250 | $B_4$ | $CH_3$ | $CH_2CH_3$ | 2-Cl | 4-Cl |
| W.251 | $B_4$ | $CH_3$ | $(CH_2)_2CH_3$ | 2-Cl | 4-Cl |
| W.252 | $B_4$ | $CH_3$ | $CH(CH_3)_2$ | 2-Cl | 4-Cl |
| W.253 | $B_4$ | H | H | 2-Cl | 6-Cl |
| W.254 | $B_4$ | H | $CH_3$ | 2-Cl | 6-Cl |
| W.255 | $B_4$ | H | $CH_2CH_3$ | 2-Cl | 6-Cl |
| W.256 | $B_4$ | H | $(CH_2)_2CH_3$ | 2-Cl | 6-Cl |
| W.257 | $B_4$ | H | $CH(CH_3)_2$ | 2-Cl | 6-Cl |
| W.258 | $B_4$ | $CH_3$ | $CH_3$ | 2-Cl | 6-Cl |
| W.259 | $B_4$ | $CH_3$ | $CH_2CH_3$ | 2-Cl | 6-Cl |
| W.260 | $B_4$ | $CH_3$ | $(CH_2)_2CH_3$ | 2-Cl | 6-Cl |
| W.261 | $B_4$ | $CH_3$ | $CH(CH_3)_2$ | 2-Cl | 6-Cl |
| W.262 | $B_4$ | H | H | 2-Cl | 8-Cl |
| W.263 | $B_4$ | H | $CH_3$ | 2-Cl | 8-Cl |
| W.264 | $B_4$ | H | $CH_2CH_3$ | 2-Cl | 8-Cl |
| W.265 | $B_4$ | H | $(CH_2)_2CH_3$ | 2-Cl | 8-Cl |
| W.266 | $B_4$ | H | $CH(CH_3)_2$ | 2-Cl | 8-Cl |
| W.267 | $B_4$ | $CH_3$ | $CH_3$ | 2-Cl | 8-Cl |
| W.268 | $B_4$ | $CH_3$ | $CH_2CH_3$ | 2-Cl | 8-Cl |
| W.269 | $B_4$ | $CH_3$ | $(CH_2)_2CH_3$ | 2-Cl | 8-Cl |
| W.270 | $B_4$ | $CH_3$ | $CH(CH_3)_2$ | 2-Cl | 8-Cl |
| W.271 | $B_4$ | H | H | 6-p-Cl-phenyl | 2-Cl |
| W.272 | $B_4$ | H | $CH_3$ | 6-p-Cl-phenyl | 2-Cl |
| W.273 | $B_4$ | H | $CH_2CH_3$ | 6-p-Cl-phenyl | 2-Cl |
| W.274 | $B_4$ | H | $(CH_2)_2CH_3$ | 6-p-Cl-phenyl | 2-Cl |
| W.275 | $B_4$ | H | $CH(CH_3)_2$ | 6-p-Cl-phenyl | 2-Cl |
| W.276 | $B_4$ | $CH_3$ | $CH_3$ | 6-p-Cl-phenyl | 2-Cl |
| W.277 | $B_4$ | $CH_3$ | $CH_2CH_3$ | 6-p-Cl-phenyl | 2-Cl |
| W.278 | $B_4$ | $CH_3$ | $(CH_2)_2CH_3$ | 6-p-Cl-phenyl | 2-Cl |
| W.279 | $B_4$ | $CH_3$ | $CH(CH_3)_2$ | 6-p-Cl-phenyl | 2-Cl |
| W.280 | $B_4$ | H | H | 8-p-Cl-phenyl | 2-Cl |
| W.281 | $B_4$ | H | $CH_3$ | 8-p-Cl-phenyl | 2-Cl |
| W.282 | $B_4$ | H | $CH_2CH_3$ | 8-p-Cl-phenyl | 2-Cl |
| W.283 | $B_4$ | H | $(CH_2)_2CH_3$ | 8-p-Cl-phenyl | 2-Cl |
| W.284 | $B_4$ | H | $CH(CH_3)_2$ | 8-p-Cl-phenyl | 2-Cl |
| W.285 | $B_4$ | $CH_3$ | $CH_3$ | 8-p-Cl-phenyl | 2-Cl |
| W.286 | $B_4$ | $CH_3$ | $CH_2CH_3$ | 8-p-Cl-phenyl | 2-Cl |
| W.287 | $B_4$ | $CH_3$ | $(CH_2)_2CH_3$ | 8-p-Cl-phenyl | 2-Cl |
| W.288 | $B_4$ | $CH_3$ | $CH(CH_3)_2$ | 8-p-Cl-phenyl | 2-Cl |

Table 7 provides 288 compounds of formula (IB), wherein A is

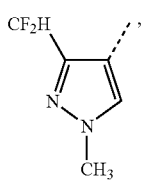

wherein the broken lines indicate the point of attachment of the group A to the amide group, and B, $R_1$, $R_2$, $R_{7d}$ and $R_{7e}$ are as defined in Table W. For example, compound 7.001 (E-form) has the following structure:

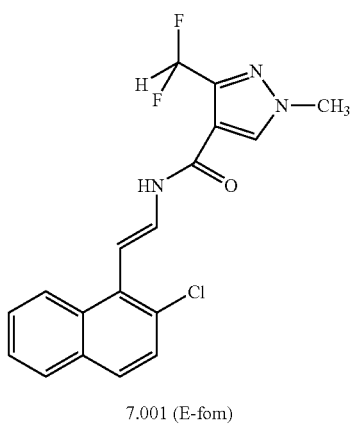

7.001 (E-fom)

Table 8 provides 288 compounds of formula (IB) wherein A is

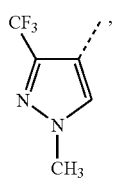

wherein the broken lines indicate the point of attachment of the group A to the amide group, and B, $R_1$, $R_2$, $R_{7d}$ and $R_{7e}$ are as defined in Table W.

Table 9 provides 288 compounds of formula (IB) wherein A is

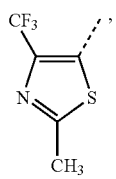

wherein the broken lines indicate the point of attachment of the group A to the amide group, and B, $R_1$, $R_2$, $R_{7d}$ and $R_{7e}$ are as defined in Table W.

Table 10 provides 288 compounds of formula (IB) wherein A is

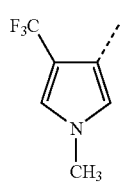

wherein the broken lines indicate the point of attachment of the group A to the amide group, and B, $R_1$, $R_2$, $R_{7d}$ and $R_{7e}$ are as defined in Table W.

Table 11 provides 288 compounds of formula (IB) wherein A is

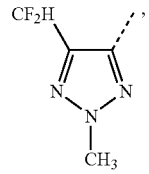

wherein the broken lines indicate the point of attachment of the group A to the amide group, and B, $R_1$, $R_2$, $R_{7d}$ and $R_{7e}$ are as defined in Table W.

Table 12 provides 288 compounds of formula (IB) wherein A is

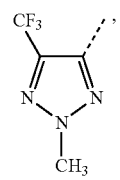

wherein the broken lines indicate the point of attachment of the group A to the amide group, and B, $R_1$, $R_2$, $R_{7d}$ and $R_{7e}$ are as defined in Table W.

Table 13: Characterising Data

Table 13 shows selected melting point and selected NMR data for compounds of Tables 1 to 12. $CDCl_3$ was used as the solvent for NMR measurements, unless otherwise stated. If a mixture of solvents was present, this is indicated as, for example: $CDCl_3/d_6$-DMSO). No attempt is made to list all characterising data in all cases.

In Table 12 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

m.p.=melting point
b.p.=boiling point.
S=singlet
br=broad
d=doublet
dd=doublet of doublets
t=triplet
q=quartet
m=multiplet
ppm=parts per million

| Comp. No. | 1H-NMR data: ppm (multiplicity/number of Hs) | MS [M + H]$^+$ | m.p. (° C.) |
|---|---|---|---|
| 1.007 (E-form) | 2.12 (d, 3H), 3.93 (s, 3H), 6.85 (t, 1H, CHF$_2$, J = 55 Hz), 7.18 (m, 2H), 7.30 (m, 2H), 7.30 (s, 1H), 7.49 (s, 1H, NH), 7.97 (s, 1H). | 326/328 | resin |
| 1.007 (Z-form) | 2.34 (d, 3H), 3.98 (s, 3H), 5.83 (s, 1H), 6.83 (t, 1H), 7.19 (m, 2H), 7.26 (m, 2H), 7.64 (s, 1H, NH), 7.84 (s, 1H). | 326/328 | resin |
| 1.024 | | | 103-105 |
| 1.025 | | | 136-137 |
| 1.079 (E-form) | 2.10 (s, 3H), 3.95 (s, 3H), 6.85 (t, 1H), 7.00 (m, 2H), 7.15-7.22 (m, 3H), 7.50 (br s, 1H), 7.97 (s, 1H). | 310 | resin |
| 1.079 (Z-form) | 2.34 (d, 3H), 3.92 (s, 3H), 5.85 (s, 1H), 6.77 (t, 1H), 7.00 (m, 2H), 7.25 (m, 2H), 7.62 (s, 1H, NH), 7.85 (s, 1H). | 310 | resin |
| 1.149 (E-form) | 2.03 (s, 3H), 3.95 (s, 3H), 6.85 (t, 1H), 7.25 (m, 3H), 7.41 (s, 1H), 7.52 (br s, 1H), 7.99 (s, 1H). | 360/362/364 | resin |
| 1.149 (Z-form) | 2.39 (d, 3H), 3.97 (s, 3H), 5.84 (s, 1H), 6.73 (t, 1H), 7.17 (dxd, 1H), 7.23 (d, 1H), 7.41 (d, 1H), 7.48 (br s, 1H), 7.84 (s, 1H). | 360/362/364 | resin |
| 2.025 | | | 145-148 |
| 2.079 (E-form) | 2.12 (s, 3H), 4.00 (s, 3H), 7.12 (br s, 1H), 7.97 (s, 1H), 7.02 (m, 2H), 7.17-7.25 (m, 3H). | 328 | 140 |
| 2.079 (Z-form) | 2.35 (s, 3H), 3.97 (s, 3H), 5.85 (s, 1H), 7.02 (m, 2H), 7.22 (m, 2H), 7.37 (br s, 1H), 7.87 (s, 1H). | 328 | 125 |

FORMULATION EXAMPLES FOR COMPOUNDS OF FORMULA I

Example F-1.1 to F-1.3

Emulsifiable Concentrates

| Components | F-1.1 | F-1.2 | F-1.3 |
|---|---|---|---|
| compound of Tables 1 to 12 | 25% | 40% | 50% |
| calcium dodecylbenzenesulfonate | 5% | 8% | 6% |
| castor oil polyethylene glycol ether (36 mol ethylenoxy units) | 50% | — | — |
| tributylphenolpolyethylene glycol ether (30 mol ethylenoxy units) | — | 12% | 4% |
| cyclohexanone | — | 15% | 20% |
| xylene mixture | 65% | 25% | 20% |

Emulsions of any desired concentration can be prepared by diluting such concentrates with water.

Example F-2

Emulsifiable Concentrate

| Components | F-2 |
|---|---|
| compound of Tables 1 to 12 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1 to 12 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1 to 12 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1 to 12 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1 to 12 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1 to 12 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

Fungicidal Actions

Example B-1

Action Against *Podosphaera leucotricha*/Apple (Powdery Mildew on Apple)

5 week old apple seedlings cv. McIntosh are treated with the formulated test compound (0.02% active ingredient) in a spray chamber. One day after application apple plants are inoculated by shaking plants infected with apple powdery mildew above the test plants. After an incubation period of 12 days at 22° C. and 60% r.h. under a light regime of 14/10 hours (light/dark) the disease incidence is assessed. Compounds 1.007 (E-from), 1.007 (Z-form), 1.024, 1.025, 1.079 (E-from), 1.079 (Z-form), 1.149 (E-from), 1.149 (Z-form), 2.025, 2.079 (E-from) and 2.079 (Z-form) show good activity in this test (<20% infestation).

Example B-2

Action Against *Venturia inaequalis*/Apple (Scab on Apple)

4 week old apple seedlings cv. McIntosh are treated with the formulated test compound (0.02% active ingredient) in a spray chamber. One day after application apple plants are inoculated by spraying a spore suspension ($4\times10^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed. Compounds 1.007 (E-from), 1.007 (Z-form), 1.024, 1.025, 1.079 (E-from), 1.079 (Z-form), 1.149 (E-from), 1.149 (Z-form), 2.025, 2.079 (E-from) and 2.079 (Z-form) show good activity in this test (<20% infestation).

Example B-3

Action Against *Erysiphe graminis*/Barley (Powdery Mildew on Barley)

1 week old barley plants cv. Express are treated with the formulated test compound (0.02% active ingredient) in a spray chamber. One day after application barley plants are inoculated by shaking powdery mildew infected plants above the test plants. After an incubation period of 6 days at 20° C./18° C. (day/night) and 60% r. h. in a greenhouse the disease incidence is assessed. Compounds 1.007 (E-from), 1.007 (Z-form), 1.024, 1.025, 1.079 (E-from), 1.079 (Z-form), 1.149 (E-from), 1.149 (Z-form), 2.025, 2.079 (E-from) and 2.079 (Z-form) show good activity in this test (<20% infestation).

Example B-4

Action Against *Botrytis cinerea*/Apple (Botrytis on Apple Fruits)

In an apple fruit cv. Golden Delicious 3 holes are drilled and each filled with 30 μl droplets of the formulated test compound (0.02% active ingredient). Two hours after application 50 μl of a spore suspension of *B. cinerea* ($4\times10^5$ conidia/ml) are pipetted on the application sites. After an incubation period of 7 days at 22° C. in a growth chamber the disease incidence is assessed. Compounds 1.007 (E-from), 1.007 (Z-form), 1.024, 1.025, 1.079 (E-from), 1.079 (Z-form), 1.149 (E-from), 1.149 (Z-form), 2.025, 2.079 (E-from) and 2.079 (Z-form) show good activity in this test (<20% infestation).

Example B-5

Action Against *Botrytis cinerea*/Grape (*Botrytis* on Grapes)

5 week old grape seedlings cv. Gutedel are treated with the formulated test compound (0.02% active ingredient) in a spray chamber. Two days after application grape plants are inoculated by spraying a spore suspension ($1 \times 10^6$ conidia/ml) on the test plants. After an incubation period of 4 days at 21° C. and 95% r.h. in a greenhouse the disease incidence is assessed. Compounds 1.007 (E-from), 1.007 (Z-form), 1.024, 1.025, 1.079 (E-from), 1.079 (Z-form), 1.149 (E-from), 1.149 (Z-form), 2.025, 2.079 (E-from) and 2.079 (Z-form) show good activity in this test (<20% infestation).

Example B-6

Action Against *Botrytis cinerea*/Tomato (*Botrytis* on Tomatoes)

4 week old tomato plants cv. Roter Gnom are treated with the formulated test compound (0.02% active ingredient) in a spray chamber. Two days after application tomato plants are inoculated by spraying a spore suspension ($1 \times 10^5$ conidia/ml) on the test plants. After an incubation period of 4 days at 20° C. and 95% r.h. in a growth chamber the disease incidence is assessed. Compounds 1.007 (E-from), 1.007 (Z-form), 1.024, 1.025, 1.079 (E-from), 1.079 (Z-form), 1.149 (E-from), 1.149 (Z-form), 2.025, 2.079 (E-from) and 2.079 (Z-form) show good activity in this test (<20% infestation).

Example B-7

Action Against *Pyrenophora teres*/Barley (Net Blotch on Barley)

1 week old barley plants cv. Express are treated with the formulated test compound (0.02% active ingredient) in a spray chamber. Two days after application barley plants are inoculated by spraying a spore suspension ($3 \times 10^4$ conidia/ml) on the test plants. After an incubation period of 2 days at 20° C. and 95% r.h. plants are kept for 2 days at 20° C. and 60% r.h. in a greenhouse. The disease incidence is assessed 4 days after inoculation. Compounds 1.007 (E-from), 1.007 (Z-form), 1.024, 1.025, 1.079 (E-from), 1.079 (Z-form), 1.149 (E-from), 1.149 (Z-form), 2.025, 2.079 (E-from) and 2.079 (Z-form) show good activity in this test (<20% infestation).

Example B-8

Action Against *Septoria tritici*/Wheat (*Septoria* Leaf Snot on Wheat)

2 week old wheat plants cv. Riband are treated with the formulated test compound (0.02% active ingredient) in a spray chamber. One day after application, wheat plants are inoculated by spraying a spore suspension ($10 \times 10^5$ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation. Compounds 1.007 (E-from), 1.007 (Z-form), 1.024, 1.025, 1.079 (E-from), 1.079 (Z-form), 1.149 (E-from), 1.149 (Z-form), 2.025, 2.079 (E-from) and 2.079 (Z-form) show good activity in this test (<20% infestation).

Example B-9

Action Against *Uncinula necator*/Grape (Powdery Mildew on Grape)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed. Compounds 1.007 (E-from), 1.007 (Z-form), 1.024, 1.025, 1.079 (E-from), 1.079 (Z-form), 1.149 (E-from), 1.149 (Z-form), 2.025, 2.079 (E-from) and 2.079 (Z-form) show good activity in this test (<20% infestation).

Example B-10

Action Against *Altemaria solani*/Tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2 \times 10^5$ conidia/ml) on the test plants. After an incubation period of 3 days at 20° C. and 95% r.h. in a growth chamber the disease incidence is assessed. Compounds 1.007 (E-from), 1.007 (Z-form), 1.024, 1.025, 1.079 (E-from), 1.079 (Z-form), 1.149 (E-from), 1.149 (Z-form), 2.025, 2.079 (E-from) and 2.079 (Z-form) show good activity in this test (<20% infestation).

What is claimed is:
1. A compound of formula I

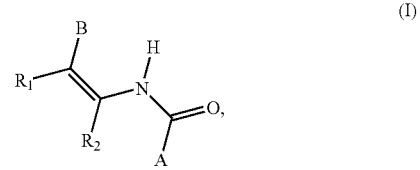

(I)

wherein
$R_1$ and $R_2$ independently of each other stand for hydrogen, halogen, nitro, $C_1$-$C_6$alkyl, which is unsubstituted or substituted by one or more substituents $R_3$, $C_3$-$C_6$cycloalkyl, which is unsubstituted or substituted by one or more substituents $R_3$, $C_2$-$C_6$alkenyl, which is unsubstituted or substituted by one or more substituents $R_3$, or $C_2$-$C_6$alkynyl, which is unsubstituted or substituted by one or more substituents $R_3$;
each $R_3$ independently of each other stands for halogen, nitro, $C_1$-$C_6$alkoxy, $C_1$-$C_6$halogenalkoxy, $C_3$-$C_6$cycloalkyl, $C_1$-$C_6$alkylthio, $C_1$-$C_6$halogenalkylthio, —C(H)=N(O—$C_1$-$C_6$alkyl) or —C($C_1$-$C_6$alkyl)=N(O—$C_1$-$C_6$alkyl);
or $R_1$ and $R_2$ together with the carbon atoms to which they are attached form a 5-, 6- or 7-membered alkene ring, wherein said ring is partially saturated and wherein said ring is unsubstituted or substituted by one or more substituents $R_4$;

each substituent $R_4$ independently of each other stands for halogen, nitro, $C_1$-$C_6$alkyl, which is unsubstituted or substituted by one or more substituents $R_5$, $C_3$-$C_6$cycloalkyl, which is unsubstituted or substituted by one or more substituents $R_5$, $C_2$-$C_6$alkenyl, which is unsubstituted or substituted by one or more substituents $R_5$, or $C_2$-$C_6$alkynyl, which is unsubstituted or substituted by one or more substituents $R_5$;

each $R_5$ independently of each other stands for halogen, nitro, $C_1$-$C_6$alkoxy, $C_1$-$C_6$halogenalkoxy, $C_3$-$C_6$cycloalkyl, $C_1$-$C_6$alkylthio, $C_1$-$C_6$halogenalkylthio, —C(H)=N(O—$C_1$-$C_6$alkyl) or —C($C_1$-$C_6$alkyl)=N(O—$C_1$-$C_6$alkyl);

A is $A_1$

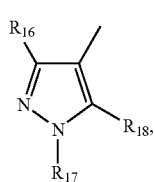

(A₁)

in which
$R_{16}$ is halogenmethyl;
$R_{17}$ is $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl; and
$R_{18}$ is hydrogen, halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

or A is $A_2$

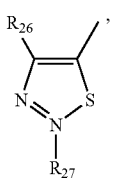

(A₂)

in which
$R_{26}$ is halogenmethyl; and
$R_{27}$ is $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl;

or A is $A_3$

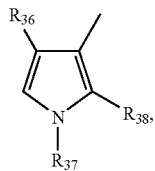

(A₃)

in which
$R_{36}$ is halogenmethyl;
$R_{37}$ is $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl; and $R_{38}$ is hydrogen, halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

B is a phenyl, naphthyl or quinolinyl group, which is substituted by one or more substituents $R_7$;

each substituent $R_7$ independently of each other stands for halogen, $C_1$-$C_6$haloalkoxy, $C_1$-$C_6$haloalkylthio, cyano, nitro, —C(H)=N(O—$C_1$-$C_6$alkyl), —C($C_1$-$C_6$alkyl)=N(O—$C_1$-$C_6$alkyl), $C_1$-$C_6$alkyl, which is unsubstituted or substituted by one or more substituents $R_8$, $C_3$-$C_6$cycloalkyl, which is unsubstituted or substituted by one or more substituents $R_8$, $C_6$-$C_{14}$bicycloalkyl, which is unsubstituted or substituted by one or more substituents $R_8$, $C_2$-$C_6$alkenyl, which is unsubstituted or substituted by one or more substituents $R_8$, $C_2$-$C_6$alkynyl, which is unsubstituted or substituted by one or more substituents $R_8$, phenyl, which is unsubstituted or substituted by one or more substituents $R_8$, or heteroaryl, which is unsubstituted or substituted by one or more substituents $R_8$;

each $R_8$ is independently of each other halogen, cyano, nitro, $C_1$-$C_6$alkoxy, $C_1$-$C_6$halogenalkoxy, $C_1$-$C_6$alkylthio, $C_1$-$C_6$halogenalkylthio, $C_3$-$C_6$alkenyloxy, $C_3$-$C_6$alkynyloxy, —C(H)=N(O—$C_1$-$C_6$alkyl) or —C($C_1$-$C_6$alkyl)=N(O—$C_1$-$C_6$alkyl);

and isomers and tautomers of the compound of formula I.

2. A compound of formula I according to claim 1, wherein A is A1.

3. A compound of formula I according to claim 1, wherein B is a phenyl group, which is substituted by one or more substituents $R_7$.

4. A compound of formula I according to claim 3, wherein each substituent $R_7$ independently of each other stands for halogen, $C_1$-$C_6$haloalkoxy, $C_1$-$C_6$haloalkylthio, cyano, nitro, —C(H)=N(O—$C_1$-$C_6$alkyl), —C($C_1$-$C_6$alkyl)=N(O—$C_1$-$C_6$alkyl), $C_1$-$C_6$alkyl, which is unsubstituted or substituted by one or more substituents $R_8$, $C_2$-$C_6$alkenyl, which is unsubstituted or substituted by one or more substituents $R_8$, or $C_2$-$C_6$alkynyl, which is unsubstituted or substituted by one or more substituents $R_8$.

5. A compound of formula I according to claim 3, wherein B is $B_1$

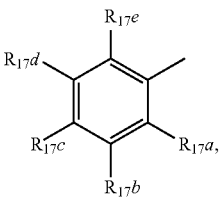

(B₁)

in which
$R_{17a}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;
$R_{17b}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;
$R_{17c}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;

$R_{17d}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens; and $R_{17e}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;

provided that at least one of $R_{17a}$, $R_{17b}$, $R_{17c}$, $R_{17d}$ and $R_{17e}$ is not hydrogen.

6. A compound of formula I according to claim 1, wherein $R_1$ and $R_2$ independently of each other stand for hydrogen, halogen or $C_1$-$C_6$alkyl, which is unsubstituted or substituted by one or more substituents selected from halogen, $C_1$-$C_6$alkoxy and $C_1$-$C_6$halogenalkoxy; or $R_1$ and $R_2$ together with the carbon atoms to which they are attached form a 5-, 6- or 7-membered alkene ring, wherein said ring is partially saturated and wherein said ring is unsubstituted or substituted by one or more substituents selected from halogen, $C_1$-$C_6$alkoxy and $C_1$-$C_6$halogenalkoxy.

7. A method of controlling infestation of useful plants by phytopathogenic microorganisms, wherein a compound of formula I according to claim 1 or a composition, comprising this compound as active ingredient, is applied to the plants, to parts thereof or the locus thereof.

8. A composition for controlling and protecting against phytopathogenic microorganisms, comprising a compound of formula I according to claim 1 and an inert carrier.

9. A compound of formula I

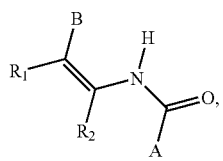

(I)

wherein $R_1$ and $R_2$ independently of each other stand for hydrogen, halogen, nitro, $C_1$-$C_6$alkyl, which is unsubstituted or substituted by one or more substituents $R_3$, $C_3$-$C_6$cycloalkyl, which is unsubstituted or substituted by one or more substituents $R_3$, $C_2$-$C_6$alkenyl, which is unsubstituted or substituted by one or more substituents $R_3$, or $C_2$-$C_6$alkynyl, which is unsubstituted or substituted by one or more substituents $R_3$;

each $R_3$ independently of each other stands for halogen, nitro, $C_1$-$C_6$alkoxy, $C_1$-$C_6$halogenalkoxy, $C_3$-$C_6$cycloalkyl, $C_1$-$C_6$alkylthio, $C_1$-$C_6$halogenalkylthio, —C(H)=N(O—$C_1$-$C_6$alkyl) or —C($C_1$-$C_6$alkyl)=N(O—$C_1$-$C_6$alkyl);

or $R_1$ and $R_2$ together with the carbon atoms to which they are attached form a 5-, 6- or 7-membered alkene ring, wherein said ring is partially saturated and wherein said ring is unsubstituted or substituted by one or more substituents $R_4$;

each substituent $R_4$ independently of each other stands for halogen, nitro, $C_1$-$C_6$alkyl, which is unsubstituted or substituted by one or more substituents $R_5$, $C_3$-$C_6$cycloalkyl, which is unsubstituted or substituted by one or more substituents $R_5$, $C_2$-$C_6$alkenyl, which is unsubstituted or substituted by one or more substituents $R_5$, or $C_2$-$C_6$alkynyl, which is unsubstituted or substituted by one or more substituents $R_5$;

each $R_5$ independently of each other stands for halogen, nitro, $C_1$-$C_6$alkoxy, $C_1$-$C_6$halogenalkoxy, $C_3$-$C_6$cycloalkyl, $C_1$-$C_6$alkylthio, $C_1$-$C_6$halogenalkylthio, —C(H)=N(O—$C_1$-$C_6$alkyl) or —C($C_1$-$C_6$alkyl)=N(O—$C_1$-$C_6$alkyl);

A is $A_1$

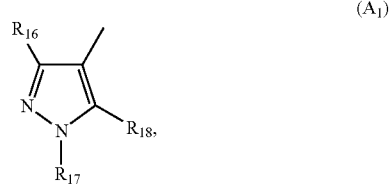

($A_1$)

in which $R_{16}$ is halogenmethyl;

$R_{17}$ is $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl; and $R_{18}$ is hydrogen, halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

B is a phenyl, naphthyl or quinolinyl group, which is substituted by one or more substituents $R_7$;

each substituent $R_7$ independently of each other stands for halogen, $C_1$-$C_6$haloalkoxy, $C_1$-$C_6$haloalkylthio, cyano, nitro, —C(H)=N(O—$C_1$-$C_6$alkyl), —C($C_1$-$C_6$alkyl)=N(O—$C_1$-$C_6$alkyl), $C_1$-$C_6$alkyl, which is unsubstituted or substituted by one or more substituents $R_9$, $C_3$-$C_6$cycloalkyl, which is unsubstituted or substituted by one or more substituents $R_8$, $C_6$-$C_{14}$bicycloalkyl, which is unsubstituted or substituted by one or more substituents $R_8$, $C_2$-$C_6$alkenyl, which is unsubstituted or substituted by one or more substituents $R_8$, $C_2$-$C_6$alkynyl, which is unsubstituted or substituted by one or more substituents $R_8$, phenyl, which is unsubstituted or substituted by one or more substituents $R_8$, or heteroaryl, which is unsubstituted or substituted by one or more substituents $R_8$;

each $R_8$ is independently of each other halogen, cyano, nitro, $C_1$-$C_6$alkoxy, $C_1$-$C_6$halogenalkoxy, $C_1$-$C_6$alkylthio, $C_1$-$C_6$halogenalkylthio, $C_3$-$C_6$alkenyloxy, $C_3$-$C_6$alkynyloxy, —C(H)=N(O—$C_1$-$C_6$alkyl) or —C($C_1$-$C_6$alkyl)=N(O—$C_1$-$C_6$alkyl);

and isomers and tautomers of the compound of formula I.

10. A compound according to claim 9, wherein B is a phenyl group, which is substituted by one or more substituents $R_7$.

11. A compound according to claim 10, wherein each substituent $R_7$ independently of each other stands for halogen, $C_1$-$C_6$haloalkoxy, $C_1$-$C_6$haloalkylthio, cyano, nitro, —C(H)=N(O—$C_1$-$C_6$alkyl), —C($C_1$-$C_6$alkyl)=N(O—$C_1$-$C_6$alkyl), $C_1$-$C_6$alkyl, which is unsubstituted or substituted by one or more substituents $R_8$, $C_2$-$C_6$alkenyl, which is unsubstituted or substituted by one or more substituents $R_8$, or $C_2$-$C_6$alkynyl, which is unsubstituted or substituted by one or more substituents $R_8$.

12. A compound according to claim 10, wherein B is $B_1$

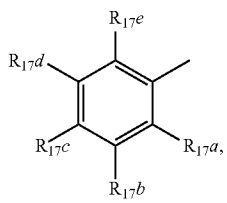
(B₁)

in which $R_{17a}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;

$R_{17b}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;

$R_{17c}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;

$R_{17d}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens; and $R_{17e}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy or phenyl, which is unsubstituted or substituted by one or more halogens;

provided that at least one of $R_{17a}$, $R_{17b}$, $R_{17c}$, $R_{17d}$ and $R_{17e}$ is not hydrogen.

13. A compound according to claim 9, wherein said compound is

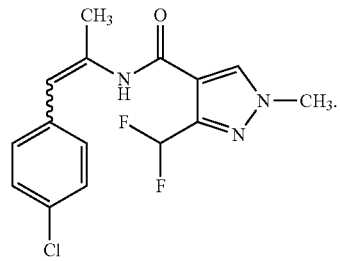

14. A composition for controlling and protecting against phytopathogenic microorganisms, comprising a compound according to claim 9 and an inert carrier.

15. A composition for controlling and protecting against phytopathogenic microorganisms, comprising a compound according to claim 11 and an inert carrier.

16. A composition for controlling and protecting against phytopathogenic microorganisms, comprising a compound according to claim 11 and an inert carrier.

17. A composition for controlling and protecting against phytopathogenic microorganisms, comprising a compound according to claim 13 and an inert carrier.

\* \* \* \* \*